(12) United States Patent
Lilley et al.

(10) Patent No.: US 11,208,694 B2
(45) Date of Patent: Dec. 28, 2021

(54) PREDICTION OF THERAPEUTIC RESPONSE IN INFLAMMATORY CONDITIONS

(71) Applicant: LIQUID BIOSCIENCE, INC., Aliso Viejo, CA (US)

(72) Inventors: Patrick Lilley, Aliso, CA (US); Matthew Nunez, Newport Beach, CA (US)

(73) Assignee: LIQUID BIOSCIENCE, INC., Aliso Viejo (GB)

( * ) Notice: Subject to any disclaimer, the term of this patent is extended or adjusted under 35 U.S.C. 154(b) by 983 days.

(21) Appl. No.: 15/845,964

(22) Filed: Dec. 18, 2017

(65) Prior Publication Data

US 2018/0142301 A1     May 24, 2018

Related U.S. Application Data

(62) Division of application No. 15/011,059, filed on Jan. 29, 2016, now Pat. No. 9,845,505.

(51) Int. Cl.
| | |
|---|---|
| *C12Q 1/6883* | (2018.01) |
| *G16B 25/10* | (2019.01) |
| *A61P 43/00* | (2006.01) |
| *G16H 50/30* | (2018.01) |
| *A61P 29/00* | (2006.01) |
| *G16B 40/00* | (2019.01) |
| *G16B 99/00* | (2019.01) |

(52) U.S. Cl.
CPC ............ *C12Q 1/6883* (2013.01); *A61P 29/00* (2018.01); *A61P 43/00* (2018.01); *G16B 25/10* (2019.02); *G16B 40/00* (2019.02); *G16H 50/30* (2018.01); *C12Q 2600/106* (2013.01); *C12Q 2600/158* (2013.01); *C12Q 2600/16* (2013.01); *G16B 99/00* (2019.02)

(58) Field of Classification Search
None
See application file for complete search history.

(56) References Cited

PUBLICATIONS

MacIsaac et al. Pre-Treatment Whole Blood Gene Expression Is Associated with 14-Week Response Assessed by Dynamic Contrast Enhanced Magnetic Resonance Imaging in Infliximab-Treated Rheumatoid Arthritis Patients PLOS ONE vol. 9, article e113937 (Year: 2014).*

* cited by examiner

*Primary Examiner* — John S Brusca
(74) *Attorney, Agent, or Firm* — Entralta P.C.; James F. Fleming; Peter D. Weinstein

(57) ABSTRACT

Response to treatment of an inflammatory condition can be predicted based on characteristics of one or more markers from a subject. The markers can include expressions of nucleotide sequences identified herein and of combinations thereof. A response value can be calculated based on characteristics (e.g., expression levels) of one or more of the markers, as well as other characteristics of the subject, such as baseline clinical data. The treatment can be administered when the response value is beyond a threshold.

25 Claims, 5 Drawing Sheets
Specification includes a Sequence Listing.

PREDICTION OF THERAPEUTIC RESPONSE IN INFLAMMATORY CONDITIONS

CROSS REFERENCE TO RELATED APPLICATIONS

This application is a divisional of U.S. application Ser. No. 15/011,059, filed Jan. 29, 2016 and now pending, which is incorporated herein by reference in its entirety.

SEQUENCE LISTING

The instant application contains a Sequence Listing that has been submitted electronically in ASCII format and is hereby incorporated by reference in its entirety. Said ASCII copy, created on Jan. 28, 2016, is named 2212089.00122US1_SL.txt and is 8,763 bytes in size.

FIELD

The subject technology relates to diagnosis and treatment of inflammatory conditions in patients, such as inflammatory arthritis. In particular, the subject technology relates to determining whether a patient will respond to one or more particular therapies.

BACKGROUND

Inflammatory arthritis is a prominent clinical manifestation in diverse autoimmune disorders including rheumatoid arthritis (RA), psoriatic arthritis (PsA), systemic lupus erythematosus (SLE), Sjogren's syndrome, and polymyositis. Most patients with these diseases develop joint deformities on physical examination, but typically only RA and PsA patients manifest bone erosions on imaging studies.

RA is a chronic inflammatory disease that affects approximately 0.5 to 1% of the adult population in northern Europe and North America, and a slightly lower proportion in other parts of the world. It is a systemic inflammatory disease characterized by chronic inflammation in the synovial membrane of affected joints, which ultimately leads to loss of daily function due to chronic pain and fatigue. The majority of patients also experience progressive deterioration of cartilage and bone in the affected joints, which may eventually lead to permanent disability. The long-term prognosis of RA is poor, with approximately 50% of patients experiencing significant functional disability within 10 years from the time of diagnosis. Life expectancy is reduced by an average of 3-10 years. Patients with a high titer of rheumatoid factor (RF) (approximately 80% of patients) have more aggressive disease, with a worse long-term outcome and increased mortality over those who are RF negative.

A common problem in caring for patients with rheumatoid arthritis is the inadequacy of current disease markers to individualize the assessment of prognosis. This is important because this inflammatory autoimmune disease often leads to chronic pain, impaired quality of life, disability, extra-articular complications and comorbidity, and increased mortality. Various approaches of predicting how patients will fare long-term have been evaluated over the years; while several have been found to be informative at the population level, few, if any, have proved sufficiently predictive at the level of individual patients to justify use in clinical practice.

SUMMARY

This document provides methods and materials related to assessing mammals (e.g., humans) with arthritis (e.g., RA). For example, this document provides methods and materials for using identifiable markers to assist clinicians in assessing RA disease activity, assessing the likelihood of response and outcomes of RA therapy, and predicting long-term RA disease outcomes.

Some embodiments of the subject technology concern the recognition that patients with RA can be selected for therapy based on the presence of certain diagnostic indicators in a sample taken from the patient. The subject technology provides diagnostic methods for predicting and/or prognosticating the effectiveness of treatment of a RA patient with an anti-TNF treatment. In particular, the subject technology concerns prediction and/or prognostication of the efficacy response to RA therapy with an anti-TNF treatment based on one or more combinations of markers.

According to some embodiments, the subject technology relates to a method for selecting a therapy for a patient or a patient population with RA. According to some embodiments, the presence, absence, and/or level of one or more markers is determined from a sample from the patient. The markers can be one or more of: a marker for suppressor of Ty 5 homolog, a marker for chromosome 1 open reading frame 105, a marker for potassium channel tetramerization domain containing 4, a marker for human cytalomegalovirus UL84, and/or a marker for Homo sapiens mRNA for T cell receptor beta chain V-D-J region. According to some embodiments, the subject technology relates to a method of treating RA in a patient comprising administering an effective amount of an anti-TNF to the patient to treat the RA.

According to some embodiments, more than one biomarker is assessed and measured from a single serum sample taken from the patient. According to some embodiments, more than one biomarker is assessed and measured from different samples taken from the patient.

According to some embodiments, the subject technology supplies a kit for predicting, diagnosing or monitoring responsiveness of a RA patient to therapy with an anti-TNF treatment, wherein the kit is calibrated to measure marker level(s) in a sample from the patient.

According to some embodiments, the amount of biomarkers may be determined by using, for example, a reagent that specifically binds with the biomarker protein or a fragment thereof, such as, e.g., an antibody, a fragment of an antibody, or an antibody derivative. The level of expression may be determined, for example, using a method selected from the group consisting of proteomics, flow cytometry, immunocytochemistry, immunohistochemistry, enzyme-linked immunosorbent assay, multi-channel enzyme-linked immunosorbent assay, and variations thereof. The expression level of a biomarker in the biological sample may also be determined by detecting the level of expression of a transcribed biomarker polynucleotide or fragment thereof encoded by a biomarker gene, which may be cDNA, mRNA or heterogeneous nuclear RNA (hnRNA). The step of detecting may include amplifying the transcribed biomarker polynucleotide, and may use the method of quantitative reverse transcriptase polymerase chain reaction. The expression level of a biomarker may be assessed by detecting the presence of the transcribed biomarker polynucleotide or a fragment thereof in a sample with a probe which anneals with the transcribed biomarker polynucleotide or fragment thereof under stringent hybridization conditions.

According to some embodiments, an antagonist is administered at a frequency of one to four doses within a period of about one month. The antagonist can be administered in two to three doses. In addition, the antagonist can be administered within a period of about 2 to 3 weeks.

According to some embodiments, the anti-TNF is administered without any other medicament to treat the RA. According to some embodiments, the method further comprises administering an effective amount of one or more second medicaments with the anti-TNF, wherein the anti-TNF is a first medicament. According to some embodiments, the medicament is optionally selected from the group consisting of anti-alpha4, etanercept, infliximab, adalimumab, kinaret, efalizumab, osteoprotegerin (OPG), anti-receptor activator of NFKB ligand (anti-RANKL), anti-receptor activator of NFKB-FC (RANK-FC), pamidronate, alendronate, actonel, zolendronate, clodronate, methotrexate (MTX), azulfidine, hydroxychloroquine, doxycycline, leflunomide, sulfasalazine (SSZ), prednisolone, interleukin-1 receptor antagonist, prednisone, and methylprednisolone.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 2. The other clauses can be presented in a similar manner.

One embodiment of the disclosed embodiments is a method of treatment. The method comprises administering to a subject in need thereof an effective amount of a medicament comprising a TNF inhibitor. The subject, prior to the administering, has a response value that is beyond a threshold indicating a predicted responsiveness of the subject to the medicament. The response value is determined by: determining, from a sample of a subject, at least two of (a) an amount of an mRNA sequence corresponding to SEQ ID NO:1, present in the sample; (b) an amount of an mRNA sequence comprising SEQ ID NO:2, present in the sample; (c) an amount of an mRNA sequence comprising SEQ ID NO:3, present in the sample; (d) an amount of an amino acid sequence comprising SEQ ID NO:4, present in the sample; or (e) an amount of an mRNA sequence of SEQ ID NO:5, present in the sample. The response value is further determined by calculating the response value based on the at least two of (a), (b), (c), (d) or (e).

In accordance with other aspects of this embodiment, the predicted responsiveness is indicated by a decrease in a DAS28 score.

In accordance with other aspects of this embodiment, the method further comprises not administering the medicament, within one month of the determining, when the response value is not beyond the threshold.

In accordance with other aspects of this embodiment, the medicament comprises infliximab, adalimumab, leflunomide, anakinra, azathioprine, cyclophosphamide, and/or etanercept.

In accordance with other aspects of this embodiment, the medicament comprises an anti-inflammatory agent.

In accordance with other aspects of this embodiment, the medicament comprises a monoclonal antibody.

In accordance with other aspects of this embodiment, the response value indicates a predicted decrease in DAS28 score within a 14 week period after administering the medicament.

In accordance with other aspects of this embodiment, the response value indicates a predicted decrease in DAS28 score by 1.2 or more within a 14 week period after commencing administering the medicament.

In accordance with other aspects of this embodiment, the threshold is 0 or a value between a first value and a second value. The first value is a mean of sample response values of a first one or more sample subjects who respond to an anti-TNF treatment. The second value is a mean of sample response values of a second one or more subjects who do not respond to the anti-TNF treatment. The sample response values for each of the sample subjects is determined based on the at least two of (a), (b), (c), (d) or (e).

In accordance with other aspects of this embodiment, the response value is determined based on (a) and (b).

In accordance with other aspects of this embodiment, when normalized, the response value is substantially equivalent to the final r[00] calculated in the sequence of operations below:
r[02]=ADD(r[5], r[2])
r[00]=ADD(r[6], r[1])
r[00]=DIV(r[2], r[0])
r[01]=SIN(r[6])
r[00]=SUB(r[0], r[1])
r[02]=MOD(r[1], r[0])
r[03]=MOD(r[4], r[0])
r[00]=SIN(r[0])
r[00]=ADD(r[2], r[0])
r[03]=MUL(r[3], r[3])
r[02]=ADD(r[6], r[3])
r[03]=DIV(r[3], r[2])
r[00]=ADD(r[3], r[0])
r[00]=ADD(r[3], r[0])
wherein:
r[5] is a normalized value of (a);
r[6] is a normalized value of (b);
r[4] is equal to 5;
r[2] is equal to 2; and
r[1] is equal to 1.

In accordance with other aspects of this embodiment, the response value is calculated based on (b) and (c).

In accordance with other aspects of this embodiment, when normalized, the response value is substantially equivalent to the final r[00] calculated in the sequence of operations below:
r[00]=SIN(r[1])
r[01]=SUB(r[1], r[0])
r[01]=SIN(r[1])
r[03]=SUB(r[6], r[1])
r[03]=SIN(r[3])
r[02]=MOD(r[4], r[3])
r[00]=SIN(r[1])
r[00]=DIV(r[6], r[0])
r[00]=MOD(r[0], r[1])
r[03]=MUL(r[3], r[0])
r[00]=SUB(r[7], r[3])
r[03]=SUB(r[6], r[0])
r[00]=SUB(r[7], r[3])
r[00]=MOD(r[0], r[1])
r[00]=ADD(r[2], r[0])
wherein:
r[1] is 1;
r[6] is a normalized value of (b);
r[4] is 5; and
r[7] is a normalized value of (c).

In accordance with other aspects of this embodiment, when normalized, the response value is substantially equivalent to the final r[00] calculated in the sequence of operations below:
r[07]=DIV(r[11], r[5])
r[04]=LN(r[13])
r[00]=DIV(r[8], r[2])
r[01]=DIV(r[7], r[4])

r[07]=MOD(r[1], r[7])
r[04]=MOD(r[0], r[7])
r[00]=SUB(r[15], r[4])
wherein:
r[11]=31;
r[5]=11;
r[13] is a normalized value of (b);
r[8]=19;
r[2]=3; and
r[15] is a normalized value of (c).

In accordance with other aspects of this embodiment, when normalized, the response value is substantially equivalent to the final r[00] calculated in the sequence of operations below:
r[07]=LOGISTICFUNC(r[15])
r[06]=DIV(r[11], r[3])
r[06]=SUB(r[13], r[6])
r[01]=DIV(r[6], r[7])
r[05]=POW(r[15], r[7])
r[00]=SUB(r[5], r[1])
wherein:
r[15] is a normalized value of (c);
r[11]=Treatment_num, wherein Treatment_num=1 if the subject is administered a drug, Treatment_num=0 if the subject is administered a placebo;
r[3]=5; and
r[13] is a normalized value of (b).

In accordance with other aspects of this embodiment, when normalized, the response value is substantially equivalent to the final r[00] calculated in the sequence of operations below:
r[02]=POW(r[7], r[2])
r[02]=MUL(r[6], r[2])
r[02]=MUL(r[6], r[2]
r[02]=MUL(r[6], r[2])
r[02]=SUB(r[4], r[2])
r[02]=POW(r[6], r[2])
r[03]=MUL(r[3], r[0])
r[03]=POW(r[3], r[0])
r[00]=SUB(r[5], r[3])
r[03]=MUL(r[5], r[3])
r[01]=SUB(r[2], r[3])
r[00]=ADD(r[0], r[0])
r[00]=ADD(r[7], r[0])
r[01]=ADD(r[1], r[0])
r[00]=DIV(r[5], r[0])
r[00]=ADD(r[1], r[0])
r[01]=DIV(r[4], r[1])
r[00]=ADD(r[0], r[0])
r[00]=ADD(r[0], r[0])
r[00]=ADD(r[1], r[0])
wherein:
r[7] is a normalized value of (a);
r[2]=Treatment_num, wherein Treatment_num=1 if the subject is administered a drug, Treatment_num=0 if the subject is administered a placebo;
r[6] is a normalized value of (c);
r[4] is a normalized value of (b);
r[3] is a normalized value of (b);
r[0]=Treatment_num, wherein Treatment_num=1 if the subject is administered a drug, Treatment_num=0 if the subject is administered a placebo;
r[5] is a normalized value of (c);

In accordance with other aspects of this embodiment, when normalized, the response value is substantially equivalent to the final r[00] calculated in the sequence of operations below:
r[06]=MUL(r[12], r[1])
r[07]=MUL(r[14], r[4])
r[07]=SUB(r[5], r[7])
r[06]=SUB(r[6], r[7])
r[00]=DIV(r[3], r[6])
r[05]=SUB(r[14], r[7])
r[02]=DIV(r[13], r[5])
r[07]=SUB(r[13], r[7])
r[00]=ADD(r[2], r[0])
r[05]=SUB(r[14], r[7])
r[02]=DIV(r[1], r[5])
r[00]=ADD(r[2], r[0])
wherein:
r[12]=Treatment_num, wherein Treatment_num=1 if the subject is administered a drug, Treatment_num=0 if the subject is administered a placebo;
r[1]=2;
r[14] is a normalized value of (a);
r[4]=7;
r[5]=11;
r[3]=5;
r[13] is a normalized value of (b); and
r[1]=2.

In accordance with other aspects of this embodiment, when normalized, the response value is substantially equivalent to the final r[00] calculated in the sequence of operations below:
r[01]=DIV(r[8], r[1])
r[05]=DIV(r[15], r[1])
r[00]=SUB(r[13], r[6])
r[07]=DIV(r[6], r[0])
r[04]=DIV(r[12], r[6])
r[05]=SUB(r[14], r[5])
r[07]=ADD(r[7], r[5])
r[05]=SUB(r[4], r[7])
r[00]=DIV(r[5], r[7])
r[07]=MUL(r[0], r[7])
r[07]=MUL(r[0], r[7])
r[00]=ADD(r[0], r[0])
r[00]=ADD(r[15], r[0])
r[00]=ADD(r[7], r[0])
wherein:
r[8]=19;
r[1]=2;
r[15]=is a normalized value of (c);
r[13] is a normalized value of (b);
r[6]=13;
r[12]=Treatment_num, wherein Treatment_num=1 if the subject is administered a drug, Treatment_num=0 if the subject is administered a placebo; and
r[14] is a normalized value of (a).

In accordance with other aspects of this embodiment, when normalized, the response value is substantially equivalent to the final r[00] calculated in the sequence of operations below:
r[03]=DIV(r[6], r[3])
r[02]=MOD(r[0], r[3])
r[01]=ADD(r[3], r[2])
r[03]=SUB(r[6], r[2])
r[02]=POW(r[6], r[1])
r[03]=ADD(r[5], r[3])
r[00]=MOD(r[3], r[2])
r[00]=SUB(r[1], r[0])
wherein:
r[6] is a normalized value of (a);
r[3]=5;
r[0]=7; and
r[5] is a normalized value of (b).

In accordance with other aspects of this embodiment, the response value is determined based on (a), and (b), and (c).

Another embodiment of the disclosed embodiments is a kit. The kit comprises an array consisting of one or more reagents for determining, from a sample of a subject, at least two at least two of (a) an amount of an mRNA sequence corresponding to SEQ ID NO:1, present in the sample; (b) an amount of an mRNA sequence comprising SEQ ID NO:2, present in the sample; (c) an amount of an mRNA sequence comprising SEQ ID NO:3, present in the sample; (d) an amount of an amino acid sequence comprising SEQ ID NO:4, present in the sample; or (e) an amount of an mRNA sequence of SEQ ID NO:5, present in the sample.

In accordance with other aspects of this embodiment, the one or more reagents are for determining, from the sample, only (a) and (b).

In accordance with other aspects of this embodiment, the one or more reagents are for determining, from the sample, only (b) and (c).

In accordance with other aspects of this embodiment, the one or more reagents are for determining, from the sample, only (a), (b) and (c).

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

DETAILED DESCRIPTION

Figure 1:
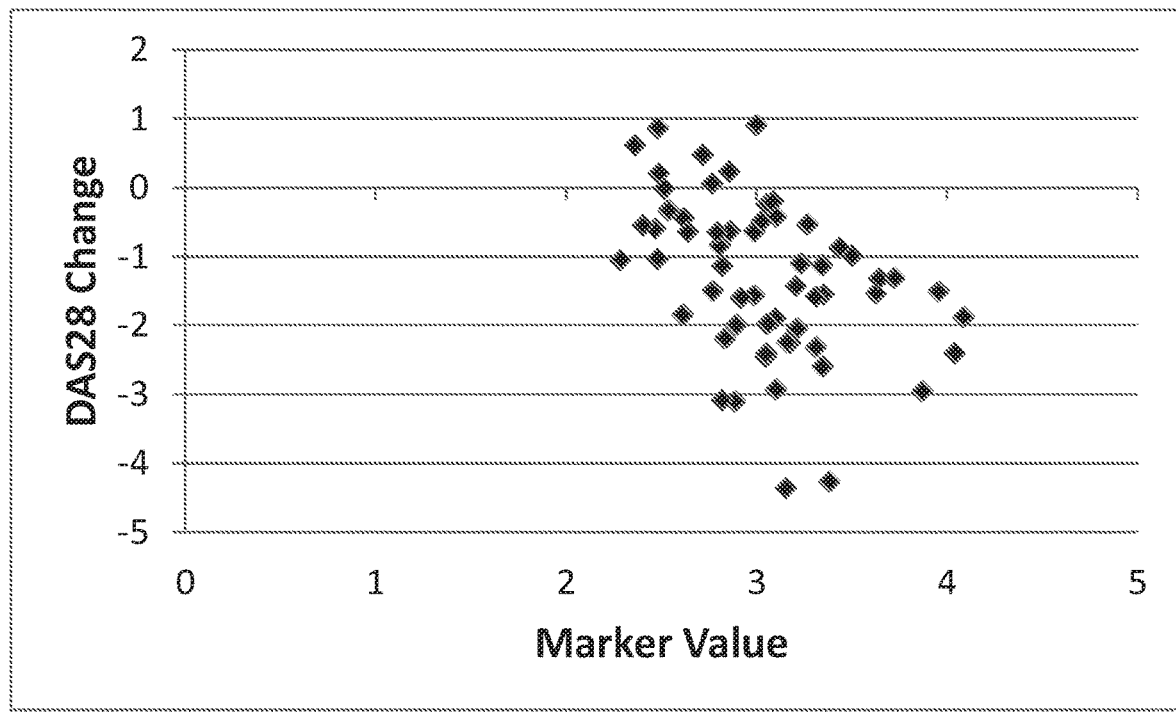
FIG. 1 shows a plot of a marker identified as SEQ ID NO:1 based on marker values (x-axis) and changes in DAS28 (y-axis) after administration of a drug.

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Definitions

The term "antibody" herein is used in the broadest sense and specifically covers monoclonal antibodies, polyclonal antibodies, multi specific antibodies (e.g. bispecific antibodies) formed from at least two intact antibodies, and antibody fragments so long as they exhibit the desired biological activity.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the subject technology may be made by a variety of techniques.

The term "anti-tumor necrosis factor antibody" or "anti-TNF" as used herein refers to an antibody that decreases, blocks, inhibits, abrogates or interferes with TNF activity in vivo. Anti-TNF antibodies useful in the methods and compositions of the subject technology include monoclonal, chimeric, humanized, resurfaced and recombinant antibodies and fragments thereof which are characterized by high affinity binding to TNF and low toxicity (including human anti-murine antibody (HAMA) and/or human anti-chimeric antibody (HACA) response). In particular, an antibody where the individual components, such as the variable region, constant region and framework, individually and/or collectively possess low immunogenicity is useful in the subject technology. The antibodies which can be used in the subject technology are characterized by their ability to treat patients for extended periods with good to excellent alleviation of symptoms and low toxicity. Low immunogenicity and/or high affinity, as well as other undefined properties, may contribute to the therapeutic results achieved.

The term "substantially similar" or "substantially the same," as used herein, denotes a sufficiently high degree of similarity between two numeric values (for example, one associated with an antibody of the subject technology and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

The term "substantially equivalent to" as used herein, denotes a sufficiently high degree of equivalence between two numeric values, such that one of skill in the art would consider the difference between the two values to be of little or no biological and/or statistical significance within the context of the measurement by said values. The difference between said two values is, for example, less than about 20%, less than about 10%, less than about 5%, and/or less than about 3%, as a function of the reference/comparator value.

As used herein, "rheumatoid arthritis" or "RA" refers to a recognized disease state that may be diagnosed according to the 2000 revised American Rheumatoid Association criteria for the classification of RA, or any similar criteria. The term includes not only active and early RA, but also incipient RA, as defined below. Physiological indicators of RA include, symmetric joint swelling which is characteristic though not invariable in RA. Fusiform swelling of the proximal interphalangeal (PIP) joints of the hands as well as metacarpophalangeal (MCP), wrists, elbows, knees, ankles, and metatarsophalangeal (MTP) joints are commonly affected and swelling is easily detected. Pain on passive motion is the most sensitive test for joint inflammation, and inflammation and structural deformity often limits the range of motion for the affected joint. Typical visible changes include ulnar deviation of the fingers at the MCP joints, hyperextension, or hyperflexion of the MCP and PIP joints, flexion contractures of the elbows, and subluxation of the carpal bones and toes. The subject with RA may be resistant to disease modifying anti-rheumatic drugs (DMARDs), in that the DMARDs are not effective or fully effective in treating symptoms. Further candidates for therapy according to this subject technology include those who have experienced an inadequate response to previous or current treatment with TNF inhibitors such as etanercept, infliximab and/or adalimumab because of toxicity or inadequate efficacy (for example, etanercept for 3 months at 25 mg twice a week or at least 4 infusions of infliximab at 3 mg/kg).

"Treatment" of a subject herein refers to both therapeutic treatment and prophylactic or preventative measures. Those in need of treatment include those already with RA or joint damage as well as those in which the RA or joint damage or the progress of RA or joint damage is to be prevented. Hence, the subject may have been diagnosed as having the RA or joint damage or may be predisposed or susceptible to the RA or joint damage, or may have RA or joint damage that is likely to progress in the absence of treatment. Treatment is successful herein if the RA or joint damage is alleviated or healed, or progression of RA or joint damage, including its signs and symptoms and structural damage, is halted or slowed down as compared to the condition of the subject prior to administration. Successful treatment further includes complete or partial prevention of RA or of the development of joint or structural damage. For purposes herein, slowing down or reducing RA or joint damage or the progression of joint damage is the same as arrest, decrease, or reversal of the RA or joint damage.

As used herein, the term "patient" refers to any single animal, more preferably a mammal (including such non-human animals as, for example, dogs, cats, horses, rabbits, zoo animals, cows, pigs, sheep, and non-human primates) for which treatment is desired. Most preferably, the patient herein is a human.

A "subject" herein is any single human subject, including a patient, eligible for treatment who is experiencing or has experienced one or more signs, symptoms, or other indicators of RA or joint damage, whether, for example, newly diagnosed or previously diagnosed and now experiencing a recurrence or relapse, or is at risk for RA or joint damage, no matter the cause. Intended to be included as a subject are any subjects involved in clinical research trials not showing any clinical sign of disease, or subjects involved in epidemiological studies, or subjects once used as controls. The subject may have been previously treated with a medicament for RA or joint damage, including an anti-TNF, or not so treated. The subject may be naïve to a second medicament being used when the treatment herein is started, i.e., the subject may not have been previously treated with, for example, an immunosuppressive agent such as MTX at "baseline" (i.e., at a set point in time before the administration of a first dose of antagonist in the treatment method herein, such as the day of screening the subject before treatment is commenced). Such "naïve" subjects are generally considered to be candidates for treatment with such second medicament.

"Clinical improvement" refers to prevention of further progress of RA or joint damage or any improvement in RA or joint damage as a result of treatment, as determined by various testing, including radiographic testing. Thus, clinical improvement may, for example, be determined by assessing the number of tender or swollen joints, the Psoriasis Assessment Severity Index, a global clinical assessment of the subject, assessing erythrocyte sedimentation rate, or assessing the amount of C-reactive protein level.

A "symptom" of RA or joint damage is any morbid phenomenon or departure from the normal in structure, function, or sensation, experienced by the subject and indicative of RA or joint damage, such as those noted above, including tender or swollen joints.

The expression "effective amount" refers to an amount of a medicament that is effective for treating RA or joint damage. This would include an amount that is effective in achieving a reduction in RA or joint damage as compared to baseline prior to administration of such amount as determined, e.g., by radiographic or other testing. An effective amount of a second medicament may serve not only to treat the RA or joint damage in conjunction with the antagonist herein, but also serve to treat undesirable effects, including side-effects or symptoms or other conditions accompanying RA or joint damage, including a concomitant or underlying disease or disorder.

A "medicament" is an active drug to treat RA or joint damage or the signs or symptoms or side effects of RA or joint damage.

A "TNF-alpha inhibitor" herein is an agent that inhibits, to some extent, a biological function of TNF-alpha, generally through binding to TNF-alpha and neutralizing its activity. Examples of TNF inhibitors specifically contemplated herein are etanercept (ENBREL®), infliximab (REMICADE®), and adalimumab (HUMIRA™). Examples of "disease-modifying anti-rheumatic drugs" or "DMARDs" include hydroxycloroquine, sulfasalazine, MTX, leflunomide, etanercept, infliximab (plus oral and subcutaneous MTX), azathioprine, D-penicillamine, gold salts (oral), gold salts (intramuscular), minocycline, cyclosporine including cyclosporine A and topical cyclosporine, staphylococcal protein A, including salts and derivatives thereof, etc. A preferred DMARD herein is MTX.

A "reagent for the determination of an indicator of expression of a nucleotide sequence" means a reagent which specifically allows for the determination of said nucleotide sequence, i.e. a reagent specifically intended for the specific determination of the expression level of the genes corresponding to the nucleotide sequence. This definition excludes generic reagents useful for the determination of the expression level of any gene, such as Taq polymerase or an amplification buffer, although such reagents may also be included in a kit according to the invention.

The term "sample" shall generally mean any biological sample obtained from an individual, body fluid, body tissue, cell line, tissue culture, or other source. Body fluids are, e.g., lymph, sera, whole fresh blood, peripheral blood mononuclear cells, frozen whole blood, plasma (including fresh or frozen), urine, saliva, semen, synovial fluid and spinal fluid. Samples also include synovial tissue, skin, hair follicle, and bone marrow. Methods for obtaining tissue biopsies and body fluids from mammals are well known in the art. If the term "sample" is used alone, it shall still mean that the "sample" is a "biological sample", i.e., the terms are used interchangeably.

The term "biomarker" as used in the present application refers generally to a DNA, RNA, protein, carbohydrate, or glycolipid-based molecular marker, the expression or presence of which in a subject's sample can be detected by standard methods (or methods disclosed herein) and is predictive or prognostic of the effective responsiveness or sensitivity of a mammalians subject with RA to an anti-TNF. Biomarkers may be present in a test sample but absent in a control sample, absent in a test sample but present in a control sample, or the amount or of biomarker can differ between a test sample and a control sample. For example, genetic biomarkers assessed (e.g., specific mutations and/or SNPs) can be present in such a sample, but not in a control sample, or certain biomarkers are seropositive in the sample, but seronegative in a control sample. Also, optionally, expression of such a biomarker may be determined to be higher than that observed for a control sample. The terms "marker" and "biomarker" are used herein interchangeably.

The terms "predictive" and "prognostic" as used herein are also interchangeable, in the sense of meaning that the methods for prediction or prognostication are to allow the person practicing the method to select patients that are deemed (usually in advance of treatment, but not necessarily) more likely to respond to treatment with an anti-TNF treatment.

The verbs "determine" and "assess" shall have the same meaning and are used interchangeably throughout the application.

An "effective response" of a patient or a patient's "responsiveness" to treatment with an anti-TNF treatment and similar wording refers to the clinical or therapeutic benefit imparted to a patient at risk for or suffering from RA from or as a result of the treatment. Such benefit includes cellular or biological responses, a complete response, a partial response, a stable disease (without progression or relapse), or a response with a later relapse of the patient from or as a result of the treatment with the antagonist. The incidence of biomarker(s) herein effectively predicts, or predicts with high sensitivity, such effective response.

The expression "not responsive to," as it relates to the reaction of subjects or patients to one or more of the medicaments that were previously administered to them, describes those subjects or patients who, upon administration of such medicament(s), did not exhibit any or adequate signs of treatment of the disorder for which they were being treated, or they exhibited a clinically unacceptably high degree of toxicity to the medicament(s), or they did not maintain the signs of treatment after first being administered such medicament(s), with the word treatment being used in this context as defined herein.

The "amount" or "level" of a biomarker associated with an increased clinical benefit to a RA patient or patient with joint damage is a detectable level in a biological sample. These can be measured by methods known to the expert skilled in the art and also disclosed by this subject technology. The expression level or amount of biomarker assessed can be used to determine the predicted responsiveness to the treatment. As used herein, an "amount" or "level" can refer to quantity, relative quantity, concentration, quantity relative to a standard, quantity relative to a quantity of another marker, quantity relative to the same marker present in a different sample, etc.

An "algorithm" as used in the methods and systems herein is a specific set of instructions or a definite list of well-defined instructions for carrying out a procedure, typically proceeding through a well-defined series of successive states, and eventually terminating in an end-state.

"Beyond" as used for "a response value beyond a threshold indicating a responsiveness of a subject to a treatment," or similar wording, refers in appropriate cases to being closer in value to a mean of response values of subjects who respond to the treatment than is a response value not beyond the threshold.

The notation "SEQ ID NO:1" when used in a calculation is a value representing an amount of SEQ ID NO:1 (i.e., an amount of an mRNA sequence comprising SEQ ID NO:1) present in a sample.

The notation "SEQ ID NO:2" when used in calculation is a value representing an amount of SEQ ID NO:2 (i.e., an amount of an mRNA sequence comprising SEQ ID NO:2) present in a sample.

The notation "SEQ ID NO:3" when used in calculation is a value representing an amount of SEQ ID NO:3 (i.e., an amount of an mRNA sequence comprising SEQ ID NO:3) present in a sample.

The notation "SEQ ID NO:4" when used in calculation is a value representing an amount of SEQ ID:4 (i.e., an amount of an amino acid sequence comprising SEQ ID NO:4) present in a sample.

The notation "SEQ ID NO:5" when used in calculation is a value representing an amount of SEQ ID NO:5 (i.e., an amount of an mRNA sequence comprising SEQ ID NO:5) present in a sample.

The notation "norm(SEQ ID NO:1)" is a value representing a normalized value of an amount of SEQ ID NO:1 (i.e., a normalized value of an amount of an mRNA sequence corresponding to SEQ ID NO:1) present in a sample.

The notation "norm(SEQ ID NO:2)" is a value representing a normalized value of an amount of SEQ ID NO:2 (i.e., a normalized value of an amount of an mRNA sequence comprising SEQ ID NO:2) present in a sample.

The notation "norm(SEQ ID NO:3)" is a value representing a normalized value of an amount of SEQ ID NO:3 (i.e., a normalized value of an amount of an mRNA sequence comprising SEQ ID NO:3) present in a sample.

The notation "norm(SEQ ID NO:4)" is a value representing a normalized value of an amount of SEQ ID:4 (i.e., a normalized value of an amount of an amino acid sequence comprising SEQ ID NO:4) present in a sample.

The notation "norm(SEQ ID NO:5)" is a value representing a normalized value of an amount of SEQ ID NO:5 (i.e., a normalized value of an amount of an mRNA sequence of SEQ ID NO:5) present in a sample.

The notation "Treatment_num" is an indicator of a value that represents whether the subject is administered, e.g., a drug or biologic (Treatment_num=1) or a placebo (Treatment_num=0).

The notation "DAS28_0" is an indicator of a value of a baseline DAS28 score.

Diagnostics

The subject technology provides a method for identifying patients whose RA or joint damage is likely to be responsive to anti-TNF therapy. The method is useful, inter alia, for increasing the likelihood that administration of an anti-TNF to a patient with RA or joint damage will be efficacious.

The methods and assays disclosed herein are directed to the examination of the amount of one or more biomarkers in a biological sample, wherein the determination of that amount of one or more such biomarkers is predictive or indicative of whether the sample will be sensitive to anti-TNFs such as antibodies or immunoadhesins.

The disclosed methods and assays provide for convenient, efficient, and potentially cost-effective means to obtain data and information useful in assessing appropriate or effective therapies for treating patients. For example, for the cytokine level determination, a patient having been diagnosed with RA could provide a blood sample and the sample could be examined by way of various in vitro assays to determine whether the patient's cells would be sensitive to a therapeutic agent that is an anti-TNF.

Methods for detecting any biomarkers desired to be assessed include protocols that examine the presence and/or expression of a desired nucleic acid, for example a SNP, in a sample. Tissue or cell samples from mammals can be conveniently assayed for, e.g., genetic-marker mRNAs or DNAs using Northern, dot-blot, or polymerase chain reaction (PCR) analysis, array hybridization, RNase protection assay, or using DNA SNP chip microarrays, which are commercially available, including DNA microarray snapshots. For example, real-time PCR (RT-PCR) assays such as quantitative PCR assays are well known in the art.

Probes used for PCR may be labeled with a detectable marker, such as, for example, a radioisotope, fluorescent compound, bioluminescent compound, a chemiluminescent compound, metal chelator, or enzyme. Such probes and primers can be used to detect the presence of a SNP in a sample and as a means for detecting a cell expressing SNP-encoded proteins. As will be understood by the skilled artisan, a great many different primers and probes may be prepared based on known sequences and used effectively to amplify, clone, and/or determine the presence and/or levels of SNP mRNAs.

Other methods include protocols that examine or detect mRNAs in a tissue or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes that have potential to be expressed in certain disease states may be arrayed on a solid support. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment.

One example of a microarray processor is the Affymetrix GENECHIP® system, which is commercially available and comprises arrays fabricated by direct synthesis of oligonucleotides on a glass surface. Other systems may be used as known to one skilled in the art.

Other methods for determining the level of the biomarker besides RT-PCR or another PCR-based method include proteomics techniques, as well as individualized genetic profiles. Individualized genetic profiles can be used to treat RA based on patient response at a molecular level. The specialized microarrays herein, e.g., oligonucleotide microarrays or cDNA microarrays, may comprise one or more biomarkers having expression profiles that correlate with either sensitivity or resistance to one or more antibodies.

For use in detection of the biomarkers, kits or articles of manufacture can also be provided by the subject technology. Such kits can be used to determine if a subject with RA will be effectively responsive to an anti-TNF. These kits may comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be an antibody or polynucleotide specific for a protein or autoantibody marker or a gene or message, respectively. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, e.g., avidin or streptavidin, bound to a reporter molecule, such as an enzymatic, florescent, or radioisotope label.

Such kit can comprise the container described above and one or more other containers comprising materials desirable from a commercial and user standpoint, including buffers, diluents, filters, needles, syringes, and package inserts with instructions for use. A label may be present on the container to indicate that the composition is used for a specific application, and may also indicate directions for either in vivo or in vitro use, such as those described above.

Other optional components of the kit include one or more buffers (e.g., block buffer, wash buffer, substrate buffer, etc.), other reagents such as substrate (e.g., chromogen) that is chemically altered by an enzymatic label, epitope retrieval solution, control samples (positive and/or negative controls), control slide(s), etc. Kits can also include instructions for interpreting the results obtained using the kit.

According to some embodiments, a kit can be configured to detect, from one or more samples, one or more markers used as inputs in a given predictive algorithm, as described herein. According to some embodiments, a kit can be configured to detect, from one or more samples, each and every marker(s) used as inputs in a given predictive algorithm, as described herein. According to some embodiments, a kit can be configured to detect, from one or more samples, only the marker(s) used as inputs in a given predictive algorithm, as described herein.

According to some embodiments, results of a detection of one or more samples can be used to determine whether the patient form whom the one or more samples was take will respond to a candidate treatment. According to some embodiments, one or more values representing indicia of one or more markers provide input(s) for an algorithm to determine whether the patient will respond to a candidate treatment.

Predictive Models

The leading drugs for rheumatoid arthritis aren't effective for 30% of patients. It has been widely believed that there are no biomarkers or prediction models that accurately identify the 30%. Various published studies have identified from 8 to 256 markers, but were not validated on additional data sets, or did not validate well (i.e., lost significant accuracy).

According to some embodiments of the subject technology, combinations of small numbers of markers (four or fewer) have been determined to discriminate response with 98.2% accuracy based on a data set of studies relating to rheumatoid arthritis. The markers have been validated against data sets, averaging 96.7% accuracy and surpassing the accuracy of the methods employed by the authors of the papers that accompany the data sets.

The following table summarizes the data sets and respective authors' results:

TABLE 1

| Journal Results | Primary (Merck) | Data Sets Used for Validation | | |
| --- | --- | --- | --- | --- |
| First Author | MacIsaac | Lequerre | Julia | Bienkowska |
| NIH Data Set ID | GSE58795 | GSE5392 | GSE12051 | GSE15258 |

TABLE 1-continued

| Journal Results | Primary (Merck) | Data Sets Used for Validation | | |
| --- | --- | --- | --- | --- |
| Publication Year | 2014 | 2006 | 2009 | 2009 |
| Subject Region/Country | Europe | France | Spain | U.S. |
| Treatment | Infliximab | Infliximab | Infliximab | Anti-TNF* |
| Subjects | 59 | 30 | 44 | 46 |
| Assay device | Affymetrix 2.0 | Agilent | Illumina H-6 | Affymetrix 2.0 |
| Type of data | mRNA | mRNA | mRNA | mRNA |
| Paper accuracy | Not provided | 90.0% | 93.2% | 89.0% |
| Paper sensitivity | Not provided | 80.0% | 94.4% | 91.0% |
| Paper specificity | Not provided | 100.0% | 85.7% | 88.0% |
| Total Number of Errors | Not provided | 3 | 3 | 5 |
| Total Number of Final Markers | 256 | 20 | 8 | 8 |
| Analytic method used | Regression | Hierarchical clustering | k-Nearest neighbors | Random forest |

*Various: Adalimumab, Etanercept, or Infliximab

For the Merck data set, this process produced a final model that used five variables: treatment/placebo, three gene expression markers, and a marker related to immune response to a strain of human cytomegalovirus (HCMV) (see Example 1). An alternate model, with nearly the same accuracy, used a baseline DAS28 measurement instead of the HCMV marker (see Example 2).

The table below shows markers that were used in the final predictive models and validation models, along with corresponding identifications and labels:

TABLE 2

| SEQ ID NO | Description | Gene Symbol |
| --- | --- | --- |
| SEQ ID NO: 1 | Suppressor of Ty 5 homolog | SPTY2D1 |
| SEQ ID NO: 2 | Chromosome 1 open reading frame 105 | C1orf105 |
| SEQ ID NO: 3 | Potassium channel tetramerization domain containing 4 | KCTD4 |
| SEQ ID NO: 4 | Marker for human cytalomegalovirus UL84 | UL84 |
| SEQ ID NO: 5 | *Homo sapiens* mRNA for T cell receptor beta chain V-D-J region | n/a |

| SEQ ID NO | Affymetrix ID | Illumina ID | Rosetta | GenBank Accession No |
| --- | --- | --- | --- | --- |
| SEQ ID NO: 1 | 100134618_TGI_at | 1558262_at | HSG00275685 | AL137366 |
| SEQ ID NO: 2 | 100146020_TGI_at | 214357_at | HSG00207321 | AL035295 |
| SEQ ID NO: 3 | 100147077_TGI_at | 239787_at | HSG00284892 | BQ575935 |
| SEQ ID NO: 4 | merck2-CMV_UL84_at | n/a | HCMV_UL84 | P16727 |
| SEQ ID NO: 5 | 100312321_TGI_at | n/a | HSG00351524 | AJ012503 |

SEQ ID NOs. 1-3 and 5 are complementary DNA (cDNA) sequences representing messenger RNA (mRNA) sequences. These cDNA sequences generally reflect the actual corresponding mRNA nucleotide sequences, replacing uracil (u) of RNA with thymidine (t) of DNA. In some embodiments, as cDNA is usually double stranded, a cDNA sequence can reflect the complement of a corresponding mRNA nucleotide sequence. As used herein, "an amount of an mRNA sequence comprising SEQ ID NO:X" where SEQ ID NO:X is a cDNA sequence, means that the cDNA sequence includes a nucleotide sequence exactly or substantially corresponding to the mRNA nucleotide sequence, replacing uracil (u) of RNA with thymidine (t) of DNA.

The following is the sequence listing for SEQ ID NO:1

```
  1  gaagctcctt agtgaggagc tgccatgctg ggccatccac catctggatt cctacgactc
 61  agggaataga acactgcacc ttccagaagc acttgtttct tcgtgggtac accaccagct
121  gagaaagaag cctcatgatg attgttgtct tatggatgct tctcattgca ggaaccatgt
181  ggaagggata taaatatccc ccaggaggga ctccagtgga agtaagcaag gatgatcctg
241  gtgaagtaat gcagctgtga agctcacctg accagctgta cagttcctgt tgttggtttc
301  acataaagta attgcacatt attttgtcat aaaaaaaaaa aaaa
```

The following is the sequence listing for SEQ ID NO:2

```
  1  atgtaaatca cacagatgtt ggtagagaaa aaggcatact ggtattgaaa ctgtaaactg
 61  gcctgtttac ttcgtctcct aacaaaaaac actttggatt caggttctcc acagcagtct
121  tccactggcc acagtgaggg gagctaggtt tccccagtct ccagctagaa aaactcagaa
181  catctaaaga tctgaaagat ggaaaaaaga gaactaaagg cttctgttcc aaaatttgac
241  aagattcctt ggcttagtga ggccagcctt gtaaacaagc cattagtgct cagccttccc
301  agaagatatc ctcatacctc tgcgactttt ctgacttcat ccaagaagaa tatgaatttg
361  ccaattttgt ttcaagttcc agatgttta tctaaggcca ggaggaacca gtgtgactcc
421  atgctgctca gaaaccaaca gctgtgctcc acatgtcaag aaatgaaaat ggtacaacca
481  agaacaatga aaatcccaga tgatccaaaa gcatcctttg agaattgtat gagttataga
541  atgagtcttc atcaacccaa attccagact acacctgagc ctttccatga tgacatccca
601  acagaaagca ttcactacag actgcccatt ctgggcccca ggacagctgt cttccacgga
661  ttactgacag aggcctacaa aactctaaaa gagagacaac gttcttcctt gcccagaaag
721  gaaccaatag gcaagacaac gaggcagtga gcggtaggag ctcatcacct cccagactcc
781  cagagagaaa ataacctcgc caagccaatc tttgacactg gcaccttctc ctcacaattt
841  tctctcttct cccaaaagat gatttaattt tgccttccta agattgctgg tattctagct
901  cttacctcta tgttctttct cacgtctcct aaagacaaaa ttgtttaatt tacatgatta
961  taaagatctg tttatgaaaa tggaa
```

The following is the sequence listing for SEQ ID NO:3

```
TTTTTTTTTTTTTTTTTAGCAAAAGCTTTCAGTCTTTATTTACAGT
ATATAGAAGGTTACTGTTTTCATTTTAGGTGGAAGAGTCTGATCAGT
AGGAACACCCCAGAGGAAGGACATCTTTAGCGATAGAATTTACATAC
CGTTAGCTCACAGTAATTGATTAGTAGCAGGGCTCTGTAGTACAGAG
CTAGCTGGGCATGTTATTTGGGATGTCTTTGATGCTGTGGTTTTCCG
AAGCTTGCTGGCTGCATGCTTGTTGCCTTTGTTCGTGACACAGGTAA
TTACTTGATAAAATGAAGTGCATCGCTGTGAACAATTGACCCTTTGG
AACAATCCAGGCTGGTCAGCAGTCTAAAGCCACACTTTAAAGCCATC
ATGATAGCCTCAAACTTAAGAGTTTCCAAGGTACAGACAAAGGTGTT
GTCTTCCTTTAGTACAAGTCGAGTGCCATTTTCAGACTTTATGAAGT
ATTTAAATTGGATGATATTTGACGATATTGAAAACTCCTCTGGAAAT
CCATCCAGCCTGCTTTTGGACACCAGAACAATGCGAGACTTTATTTT
TGATATGAAATCAGGAGCATTACAGAAGATTCTTAATCCTTGTGAAC
GATCGTGGTTATCTGTTATTTCCAAGAAAGTAGTCTCTCTGGGTGTT
AGCTGTTCTTTCTCCCACCTGGATNTCACTTCCTCTGCCAGTCNCTT
GAGCTGAAAGATTCTGC
```

The following is the sequence listing for SEQ ID NO:4

```
  1  mprvdpnlrn rarrprarrg ggggvgsnss rhsgkcrrqr ralsappltf lattttttmm
 61  gvastdddsl llktpdeldk ysgspqtilt ltdkhdirqp rvhrgtyhli qlhldlrpee
121  lrdpfqills tplqlgeand esqtapatlq eeetaashep ekkkekqekk eededdrndd
```

```
-continued
181    rergilcvvs nedsdvrpaf slfparpgch ilrsvidqql trmaivrlsl nlfalriitp 241    llkrlplrrk aahhtalhdc lalhlpeltf eptldinnvt enaasvadta estdadltpt 301    ltvrvrhalc whrveggisg prgltsrisa rlsettaktl gpsvfgrlel dpnesppdlt 361    lssltlyqdg ilrfnvtcdr teapadpvaf rlrlrretvr rpffsdaplp yfvpprsgaa 421    deglevrvpy eltlknshtl riyrrfygpy lgvfvphnrq glkmpvtvwl prswleltvl 481    vsdengatfp rdallgrlyf isskhtlnrg clsamthqvk stlhsrstsh spsqqqlsvl 541    gasialedll pmrlaspete pqdckltent tektspvtla mvcgdl
```

Each amino acid in the sequence listing for SEQ ID NO:4 is represented as one letter under the International Union of Pure and Applied Chemistry (IUPAC) standard, and can be converted to three letters, according to the following well-recognized conversion scheme:

| Amino acids | | Symbols |
|---|---|---|
| Alanine | Ala | A |
| Cysteine | Cys | C |
| Aspartic acid | Asp | D |
| Glutamic acid | Glu | E |
| Phenylalanine | Phe | F |
| Glycine | Gly | G |
| Histidine | His | H |
| Isoleucine | Ile | I |
| Lysine | Lys | K |
| Leucine | Leu | L |
| Methionine | Met | M |
| Asparagine | Asn | N |
| Proline | Pro | P |
| Glutamine | Gln | Q |
| Arginine | Arg | R |
| Serine | Ser | S |
| Threonine | Thr | T |
| Valine | Val | V |
| Tryptophan | Trp | W |
| Tyrosine | Tyr | Y |

The following is the sequence listing for SEQ ID NO:5

```
1      ggaaccaatc caaatgccca tcaatgatag actagataaa gaaaatatag tacatatgca 61     ccatgtaata ctatgcagcc gtaaaaaaaa aaaaaaaaaa agacagacaa ggccaaggcc 121    aggcacggtg ggtaaaaaaa aaaa
```

As shown in FIG. 1, the marker identified as SEQ ID NO:1, for given marker values (x-axis) in accordance with the data sets analyzed, provided corresponding changes in DAS28 (y-axis) after administration of a drug. This marker was determined to have a positive associate with drug response. The correlation coefficient was determined to be −0.44.

Figure 2:
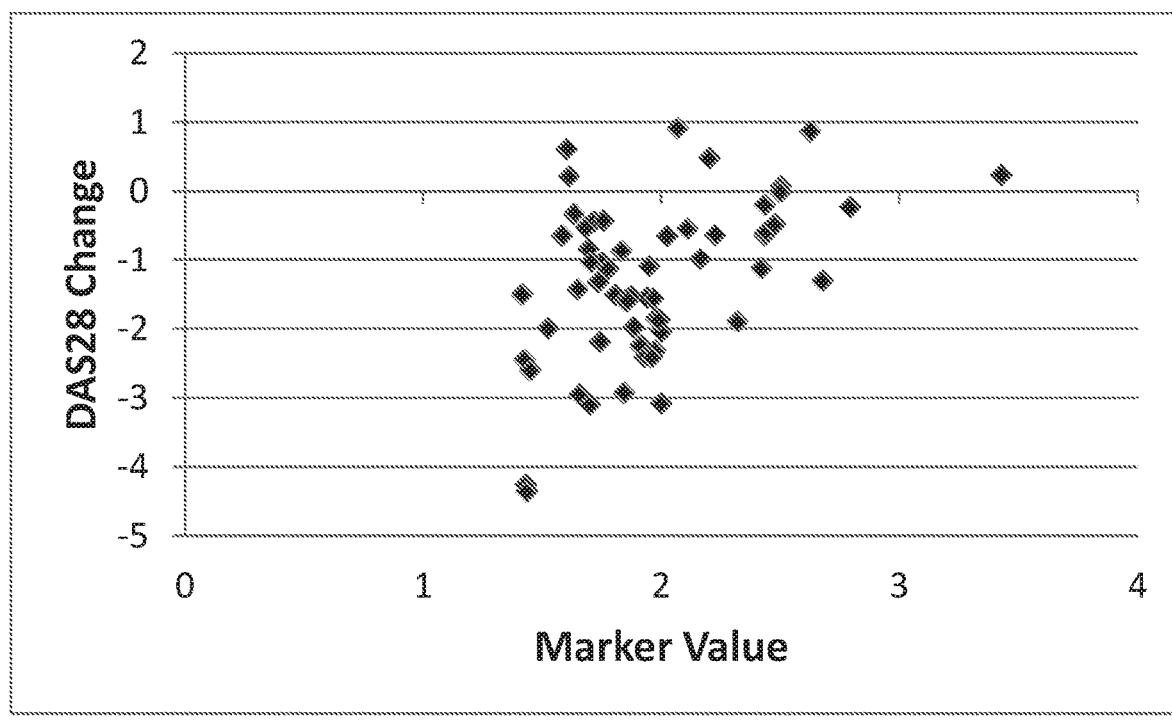
FIG. 2 shows a plot of a marker identified as SEQ ID NO:2 based on marker values (x-axis) and changes in DAS28 (y-axis) after administration of a drug.

As shown in FIG. 2, the marker identified as SEQ ID NO:2, for given marker values (x-axis) in accordance with the data sets analyzed, provided corresponding changes in DAS28 (y-axis) after administration of a drug. This marker was determined to have a negative associate with drug response. The correlation coefficient was determined to be +0.47.

Figure 3:
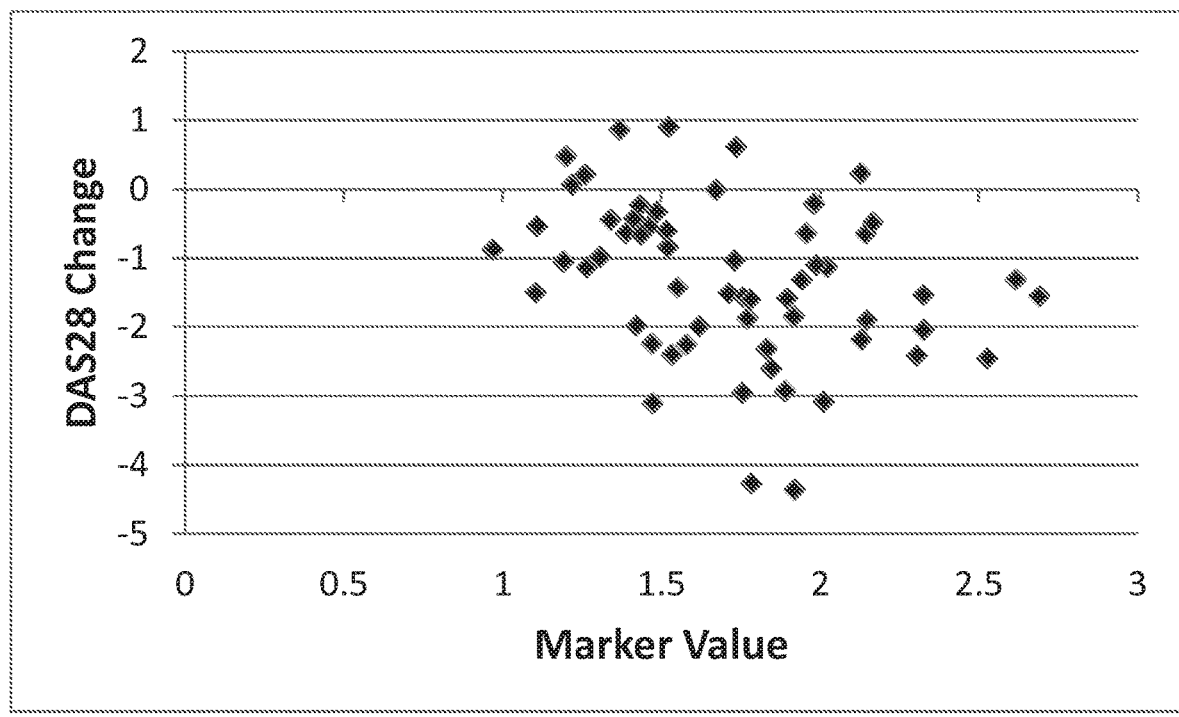
FIG. 3 shows a plot of a marker identified as SEQ ID NO:3 based on marker values (x-axis) and changes in DAS28 (y-axis) after administration of a drug.

As shown in FIG. 3, the marker identified as SEQ ID NO:3, for given marker values (x-axis) in accordance with the data sets analyzed, provided corresponding changes in DAS28 (y-axis) after administration of a drug. This marker was determined to have a positive associate with drug response. The correlation coefficient was determined to be −0.33.

Figure 4:
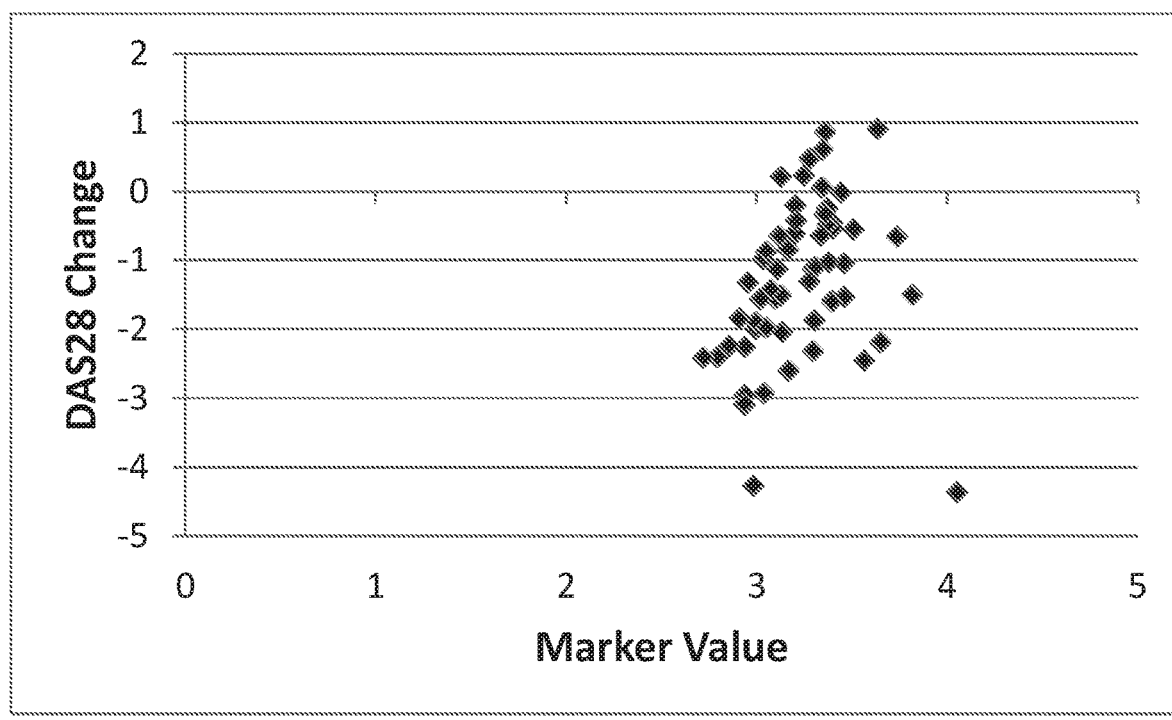
FIG. 4 shows a plot of a marker identified as SEQ ID NO:4 based on marker values (x-axis) and changes in DAS28 (y-axis) after administration of a drug.

As shown in FIG. 4, the marker identified as SEQ ID:NO4, for given marker values (x-axis) in accordance with the data sets analyzed, provided corresponding changes in DAS28 (y-axis) after administration of a drug. This marker was determined to have a negative associate with drug response. The correlation coefficient was determined to be +0.25.

In order to validate the sets of markers, we obtained three additional data sets of gene expression markers for rheumatoid arthritis patients using anti-TNF drugs. These data sets were discussed in papers by Lequerre (2006) (see Example 3), Julia (2009) (see Example 4), and Bienkowska (2009) (see Example 5).

The three validation data sets were analyzed using the same approach employed for the Merck data set, using only the final variables that emerged from the Merck analysis or a subset thereof. Some of these variables were not available in the validation data sets. The HCMV marker was not available in any validation data set. The baseline DAS28 was only available in Bienkowska. One of the three expression markers was not available in Lequerre. None of the three validation sets had any placebo subjects. The table below shows which variables were used in each of the models generated:

TABLE 3

| Variables Considered | Primary (Merck) | Data Sets Used for Validation | | |
|---|---|---|---|---|
| First Author | MacIsaac | Lequerre | Julia | Bienkowska |
| Example | 1 | 2 | 3 | 4 | 5 |
| Baseline RAS28 | | X | Not in data set | Not in data set | X |
| Treatment vs. Placebo | X | X | N/A | N/A | N/A |
| SEQ ID NO: 1 | X | X | | | |
| SEQ ID NO: 2 | X | X | X | | |
| SEQ ID NO: 3 | X | X | Not in data set | X | X |
| SEQ ID NO: 4 | X | | Not in data set | Not in data set | Not in data set |

The table below shows the results of each of the models as applied to the corresponding data sets:

TABLE 4

| Results | Primary (Merck) | Data Sets Used for Validation | | |
|---|---|---|---|---|
| | | Lequerre | Julia | Bienkowska |
| First Author | MacIsaac | Lequerre | Julia | Bienkowska |
| Accuracy-- Training | 96.7% | 100.0% | 100.0% | 91.3% |
| Accuracy-- Validation | 100.0% | 100.0% | 100.0% | 91.7% |
| Accuracy-- Test | 100.0% | 100.0% | 90.9% | 100.0% |
| Accuracy-- Overall | 98.3% | 100.0% | 97.7% | 93.5% |
| Sensitivity | 96.7% | 100.0% | 100.0% | 100.0% |
| Specificity | 100.0% | 100.0% | 85.7% | 86.4% |
| Total Number of Errors | 1 | — | 1 | 3 |
| Total Number of Final Markers | 4 | 1 | 1 | 1 |

For all four data sets, the accuracy of the models described herein was greater than that of the models discussed in the papers, and the number of explanatory variables was much smaller.

While multiple markers contributed to achieving maximum accuracy in the Merck data set, each of the validation set models used only a single gene expression marker (our model for Bienkowska also used the baseline DAS28 score). The single marker was not always the same marker across all three data sets. It may be that two of the final three markers are similarly and independently effective in discriminating responders versus non-responders.

For the Lequerre, and Julia data sets, which were both Infliximab studies, accuracy remained consistent with the Merck model, despite the Merck, Lequerre, and Julia data sets having different subject geographies, as well as using three different gene expression assay devices over an eight-year evolving period of the state of the art in such assays. For the Bienkowska data set, our model's accuracy was 93.5% versus the 98.3% for the Merck data set. This may be accounted for by the Bienkowska data set including three anti-TNF drugs, not just Infliximab.

A number of factors pointed to the validity of the markers and models. Consistent accuracy across data sets indicates that the markers had generalized utility. Consistent accuracy across training, validation, and test subsets of the data indicates that the models are unlikely to be brittle (fall apart on data sets generated in the same way). One variable in the Merck data set was placebo versus treatment. This variable emerged because of its utility, not because of a hypothesis or forced inclusion. Another variable that emerged agnostically from the Merck data set was related to a strain of the HCMV virus, which is referenced in a 2013 Mayo Clinic paper as being implicated in arthritis, and also in a 2009 immunosenescence paper by collaborators from King's College London, Cardiff University, the University of Palermo, and Tubingen Medical School, Germany. Of the 52,379 variables in the Merck data set, only five emerged in the final model, which indicates a low likelihood of spurious curve-fitting. In the model for each of the smaller validation data sets, only one or two of the five variables were necessary, indicating that each of those variables has high predictive value independent of the others. All of the final models were parsimonious (comprised of few transforms), indicating low likelihood of spurious curve-fitting. When examined in visual XY plots versus DAS28 change, all of the biomarkers showed patterns that were discernable to the human eye, though it should be noted that none of the variables would have ranked highly by correlation (due to either nonlinear patterns or heteroscedasticity that rendered them less salient to linear discriminants that are typically used for feature selection). None of the biomarkers we discovered were mentioned in any of the four papers.

Each of these results is described in further detail in the examples below.

Example 1

In 2014, Merck published a PLOS One paper on identifying gene expression markers for patient response to Infliximab (see MacIsaac K D, Baumgartner R, Kang J, Loboda A, Peterfy C, et al. (2014) Pre-Treatment Whole Blood Gene Expression Is Associated with 14-Week Response Assessed by Dynamic Contrast Enhanced Magnetic Resonance Imaging in Infliximab-Treated Rheumatoid Arthritis Patients. PLoS ONE 9(12):e113937. doi: 10.1371/journal.pone.0113937). The study involved 59 European subjects (30 responders and 29 non-responders), for each of which 52,378 gene expression markers (from Affymetrix 2.0 device) were collected, along with other metadata. Responders were defined as reduction in Disease Activity Score of 28 joints ("DAS28") of 1.2 or more by 14 weeks after baseline.

Disease Activity Score of 28 joints is used as an indicator of RA disease activity and response to treatment. The joints included in DAS28 are (bilaterally): proximal interphalangeal joints (10 joints), metacarpophalangeal joints (10), wrists (2), elbows (2), shoulders (2) and knees (2). When looking at these joints, both the number of joints with tenderness upon touching (TEN28) and swelling (SW28) are counted. In addition, the erythrocyte sedimentation rate (ESR) is measured. Also, the affected person makes a subjective assessment (SA) of disease activity during the preceding 7 days on a scale between 0 and 100, where 0 is "no activity" and 100 is "highest activity possible". With these parameters, DAS28 is calculated as:

$$DAS28 = 0.56 \times \sqrt{TEN28} + 0.28 \times \sqrt{SW28} + 0.70 \times \ln(ESR) + 0.014 \times SA$$

In the MacIsaac study, blood was collected at baseline and genome-wide transcription in whole blood was measured using microarrays. The primary endpoint in the study was determined by measuring the transfer rate constant ($K_{trans}$) of a gadolinium-based contrast agent from plasma to synovium using MM. Secondary endpoints included repeated clinical assessments with DAS28(CRP), and assessments of osteitis and synovitis by the RAMRIS method. Infliximab showed greater decrease from baseline in DCE-MRI $K_{trans}$ of wrist and MCP at all visits compared with placebo (P<0.001). Statistical analysis was performed to identify genes associated with treatment-specific 14-week change in $K_{trans}$. The 256 genes identified were used to derive a gene signature score by averaging their log expression within each patient.

RNA was isolated from PAXgene blood samples (2.5 ml) according to the manufacturer's instructions. Isolated total RNA samples were assayed for quality (Agilent Bioanalyzer) and yield (Ribogreen) metrics prior to amplification. Fifty-nine samples passing quality control (QC) were then amplified using the NuGEN Ovation WB protocol and hybridized to Rosetta/Merck Human RSTA Custom Affymetrix 2.0 microarrays. Microarray data have been deposited in the Gene Expression Omnibus archive (GEO accession GSE58795).

QC analysis was performed in the absence of treatment allocation information. QC metrics, including average background signal, scale factor, beta-actin and GAPDH 3' to 5' ratios, and the number of genes called "present" using the MASS algorithm, were examined to assess potential technical quality issues related to amplification and RNA degradation. No problematic samples were identified. Array probe intensity normalization was performed using the RMA algorithm in R/Bioconductor. Gene expression patterns and their principal components of variation were checked against the principal components of sample quality and process parameters (QC). The first two QC principal components were observed to correlate significantly with several principal components of variation in the expression data. Therefore, prior to further analysis, the RMA-normalized expression data was detrended by regressing the log 2 intensity of each probe set against the first two QC principal components.

Placebo subjects comprised 49% of the subjects in the MacIsaac study. The authors used ordinary least squares regression to identify 256 markers implicated in response. No accuracy figures were provided. Merck made the gene expression data set available on the NIH web site, under ID GSE58795, but did not include any subject demographics or other metadata.

The GSE58795 data set was downloaded and a model was generated that predicted responders versus non-responders with 98.3% accuracy (96.7% sensitivity and 100% specificity). The data set was analyzed and the models were generated using software that produces algorithmic models that are essentially stacks of signal processors. Each signal processor may be a linear, nonlinear, or discrete transform, and may operator on single or combined explanatory variables. The software evolves tens of thousands of these models in an accelerated, virtual ecosystem. Model fitness, and therefore survival and propagation, is governed by the problem definition. Therefore, the process is agnostic and requires no hypothesis or domain expertise. This approach efficiently handles massive dimensionality and reduces millions of available variables to the handful that matter, revealing the nature of the relationships governing the mechanism being modeled.

In order to avoid over-fitting and aid in the removal of low-utility and spurious variables, the software separated the data set into subsets for different purposes. For example, for the Merck data set, the software evolved a population of predictive models using 30 of the 59 total subject records. An additional 15 records were used for validation and selection of a single predictive model. The selected model was then tested against a final hold-out sample of 14 records, to verify that it holds up on new, real-world data.

The following mathematical operators were used to generate the instructions in the models:

| Operator | Description |
|---|---|
| ADD (x, y) | x + y |
| ATAN2(x) | ATAN2 - Arctangent(x, y) |
| CONSTADD (A, B) | constant A + constant B |
| COS (x) | cosine(x) (x in radius) |
| DIV (x, y) | x/y |
| EXP (x) | e (Euler's number 2.71828 . . .) raised to the power of x |
| FLOOR(x) | FLOOR - Floor function |
| IF (expression) | IF -- evaluates truth of expression. If true, the following instruction is executed, otherwise skipped. |
| MOD (x, y) | Double-precision modulo - remainder of x/y (can be non-integer) |
| MUL (x, y) | x multiplied by y |
| POW (x, y) | x raised to the power of y |
| SIN(x) | Sine(x) (x in radians) |
| SUB (x, y) | x - y |

-continued

| Operator | Description |
|---|---|
| LN(x) | Natural logarithm of x |
| LOGISTICFUNC (x) | 1/(1 + e raised to the power of -x) |

For each step, an instruction is provided as a mathematical operation. Each register value (i.e., r[x]) in a given instruction is provided by inputs provided in the "Notation" column or by the solution for the register value in a step that precedes the given instruction. For example, a value of r[03] in an instruction of Step 2 is provided by a solution for r[03] in Step 1. Where multiple solutions for a given register value appear in preceding steps, the solution for the given register most immediately preceding step is used. For example, where solutions for r[05] are provided in Steps 5 and 6, a value of r[05] in an instruction of Step 8 is provided by the solution for r[05] in Step 6, rather than that of Step 5.

According to some embodiments, a model for determining whether a subject would have a response to a candidate treatment can include the following steps:

| Step Number | Instruction | Notation |
|---|---|---|
| 1 | r[03] = DIV(r[12], r[4]) | r[12] = SEQ ID NO: 3, r[4] = 3 |
| 2 | r[05] = ADD(r[11], r[3]) | r[11] = SEQ ID NO: 2 |
| 3 | r[00] = SUB(r[12], r[5]) | r[12] = SEQ ID NO: 3 |
| 4 | r[04] = MUL(r[0], r[5]) | |
| 5 | r[06] = ADD(r[4], r[5]) | |
| 6 | r[06] = MUL(r[15], r[6]) | r[15] = Treatment_num |
| 7 | r[05] = ADD(r[10], r[6]) | r[15] = Treatment_num |
| 8 | r[04] = SUB(r[14], r[5]) | r[15] = Treatment_num |
| 9 | r[03] = DIV(r[12], r[4]) | r[10] = SEQ ID NO: 1 |
| 10 | r[05] = ADD(r[11], r[3]) | r[10] = SEQ ID NO: 1 |
| 11 | r[00] = SUB(r[10], r[5]) | r[14] = SEQ ID NO: 4 |
| 12 | r[03] = DIV(r[12], r[4]) | r[12] = SEQ ID NO: 3 |
| 13 | r[05] = ADD(r[11], r[3]) | r[11] = SEQ ID NO: 2 |
| 14 | r[00] = SUB(r[12], r[5]) | r[10] = SEQ ID NO: 1 |

In some embodiments, where r[00]≥0, a determination can be made that the subject would have a response (i.e., would be a responder) to a candidate treatment, and where r[00]<0, a determination can be made that the subject would not have a response (i.e., would be a non-responder) to the candidate treatment. For example, following the last operation above, the above model can further include a step including the instruction: if r[00]≥0, then the subject would have a response (i.e., would be a responder) to a candidate treatment; if r[00]<0, the subject would not have a response (i.e., would be a non-responder) to the candidate treatment.

The response value, r[00], compared to the threshold, 0, indicates a responsiveness of the subject to a candidate treatment by a predicted decrease in DAS28 score. As used in this model, "response" is defined as a decline in DAS28 of greater than 1.2 by 14 weeks after baseline.

For the above and all other models described herein, alternate models with an equivalent result are also contemplated. It will be recognized that variations in a model can be made while providing an equivalent result. For any given set of inputs (e.g., markers), an alternate model can achieve a result that is equivalent to the result of the given model even if the alternate model (i) performs the same steps in a different order, (ii) applies different instructions, (iii) applies different constants, (iv) omits one or more of the steps, and/or (v) includes one or more steps in addition to the steps. For example, an alternate model, relative to the given model, can include an omission, addition, and/or modification of one or more of the steps and produce an equivalent result for a given set of inputs defined by markers. An input that is not defined by the subject (e.g., constants) can be varied with a corresponding change in the instructions to produce an equivalent result. An input that is defined by the subject (e.g., markers from a sample) can be scaled or measured differently with a corresponding change in the instructions to produce an equivalent result. Such variations, inter alia, are contemplated by the given model and considered equivalent to the given model at least in the result. Results of two models are "equivalent" if, for any given subject, the final value or determination (e.g., relating to r[00]) would be the same between the two models. Results of two models are "substantially equivalent" if, for a population of subjects, the final values or determinations (e.g., relating to r[00]) would be the same for at least 99%, at least 95%, and/or at least 90% of the members of the population.

Example 2

An alternate model, with nearly the same accuracy as the model in Example 1, used a baseline DAS28 measurement instead of the HCMV marker. The alternate model was generated based on the same data set (GSE58795 data set) as that used in Example 1.

According to some embodiments, a model for determining whether a subject would have a response to a candidate treatment can include the following steps:

| Step Number | Instruction | Notation |
|---|---|---|
| 1 | r[04] = SUB(r[10], r[2]) | r[10] = SEQ ID NO: 1, r[2] = 2 |
| 2 | r[06] = MUL(r[12], r[4]) | r[12] = SEQ ID NO: 3 |
| 3 | r[00] = MUL(r[5], r[1]) | r[5] = −1, r[1] = 1 |
| 4 | r[01] = SUB(r[0], r[7]) | r[7] = 7 |
| 5 | r[07] = MUL(r[15], r[6]) | r[15] = DAS28_0 |
| 6 | r[06] = SUB(r[12], r[1]) | r[12] = SEQ ID NO: 3 |
| 7 | r[05] = SUB(r[13], r[6]) | r[13] = SEQ ID NO: 5 |
| 8 | r[06] = ADD(r[13], r[7]) | r[13] = SEQ ID NO: 5 |
| 9 | r[00] = MUL(r[11], r[5]) | r[11] = SEQ ID NO: 2 |
| 10 | r[00] = ADD(r[6], r[0]) | |
| 11 | r[00] = ADD(r[14], r[0]) | r[14] = Treatment_num |
| 12 | r[00] = ADD(r[0], r[0]) | |

In some embodiments, where r[00]≥0, a determination can be made that the subject would have a response (i.e., would be a responder) to a candidate treatment, and where r[00]<0, a determination can be made that the subject would not have a response (i.e., would be a non-responder) to the candidate treatment. For example, following the last operation above, the above model can further include a step including the instruction: if r[00]≥0, then the subject would have a response (i.e., would be a responder) to a candidate treatment; if r[00]<0, the subject would not have a response (i.e., would be a non-responder) to the candidate treatment.

The response value, r[00], compared to the threshold, 0, indicates a responsiveness of the subject to a candidate treatment by a predicted decrease in DAS28 score. As used in this model, "response" is defined as a decline in DAS28 of greater than 1.2 by 14 weeks after baseline.

Example 3

In order to validate the sets of markers, we obtained an additional data set of gene expression markers for rheumatoid arthritis patients using anti-TNF drugs as discussed in Lequerre T, Gauthier-Jauneau A-C, Bansard C, et al. Gene profiling in white blood cells predicts infliximab responsiveness in rheumatoid arthritis. *Arthritis Research & Therapy.* 2006; 8(4):R105. doi:10.1186/ar1990.

In Lequerre, 33 patients with very active disease (Disease Activity Score 28>5.1) that resisted weekly methotrexate therapy were given infliximab at baseline, weeks 2 and 6, and every 8th week thereafter. The patients were categorized as responders if a change of Disease Activity Score 28=1.2 was obtained at 3 months. Mononuclear cell RNAs were collected at baseline and at three months from responders and non-responders. The baseline RNAs were hybridised to a microarray of 10,000 non-redundant human cDNAs. In 6 responders and 7 non-responders, 41 mRNAs identified by microarray analysis were expressed as a function of the response to treatment and an unsupervised hierarchical clustering perfectly separated these responders from non-responders. The informativeness of 20 of these 41 transcripts, as measured by qRT-PCR, was re-assessed in 20 other patients. The combined levels of these 20 transcripts properly classified 16 out of 20 patients in a leave-one-out procedure, with a sensitivity of 90% and a specificity of 70%, whereas a set of only 8 transcripts properly classified 18/20 patients.

The PBMCs were isolated from venous blood by Ficoll-Hypaque centrifugation and total RNAs were extracted by a standard phenol/chloroform procedure, quality controlled on an Agilent 2100 Bioanalyzer (Agilent Technologies, Palo Alto, USA) and frozen at −80° C. until further use. An internal, arbitrary standard was made of a mixture of total RNAs from PBMCs taken from three healthy donors. The oligodT-primed poly(A) mRNAs were labelled with [α33P] dCTP, and the resulting, labelled cDNAs were immediately used for hybridisation.

Complementary DNA probes were selected on the basis of a tissue-preferred expression in liver corresponded to genes with a liver-restricted expression (10% of the probes) as well as genes with a hepatic expression along with a broad expression in some (50%) or many non-hepatic tissues (40%). All arrays were made from a single batch of cDNA probes. Every RNA sample was hybridised at least twice on separate arrays. Whenever necessary, the sequence of cDNA probes was controlled with an ABI3100 capillary sequencer (Applied Biosystems APPLERA-France, Courtaboeuf, France). Real-time, quantitative reverse transcription PCR (qRT-PCR) of mRNAs and normalization with the 18S RNA amount were done in duplicate as described.

Image analysis with the XDotsReader software, version 1.8 (COSE, Le Bourget, France), subtractions of noise and spot background, and image normalization with the median value of all signals per image were done exactly as previously detailed. A transcript was considered to be expressed if at least two hybridisations provided a positive signal. The resulting, normalized values were used for a selection of significantly regulated mRNAs, that is, those with an abundance that differed in two or more comparisons between two samples, using a funnel-shaped confidence interval (p<0.05) calculated from every mRNA detected per hybridisation. This results in a false discovery rate that is below 10% of the total number of regulated mRNAs. Statistical analyses were done with the R software. The TIGR Multiexperiment viewer (Tmev version 2.2) was used for unsupervised hierarchical clustering (HC) using the average dot product and complete linkage options, the leave-one-out cross-validation, and the supervised statistical tool Significance Analysis of Microarrays (SAM) for identification of discriminant transcripts with a false discovery rate set at <1%. Information about our clinical and experimental data complies with the recommendations for the minimum information about microarray experiments (MIAME) and the raw data have been deposited (accession number GSE3592) in the GEO repository.

The validation data set of Lequerre was analyzed using the same approach employed for the Merck data set, using only the final variables that emerged from the Merck analysis or a subset thereof (see Examples 1 and 2). One of the expression markers from the Merck data set was not available in Lequerre. The Lequerre data set had no placebo subjects.

According to some embodiments, a model for determining whether a subject would have a response to a candidate treatment can include the following steps:

| Step Number | Instruction | Notation |
|---|---|---|
| 1 | r[02] = ADD(r[3], r[2]) | r[3] = 13, r[2] = 7 |
| 2 | r[03] = MUL(r[7], r[2]) | r[7] = SEQ ID NO: 2 |
| 3 | r[02] = POW(r[3], r[2]) | |
| 4 | r[02] = SIN(r[2]) | |
| 5 | r[02] = SIN(r[2]) | |
| 6 | r[03] = FLOOR(r[3]) | |
| 7 | r[00] = SIN(r[3]) | |
| 8 | r[03] = ATAN2(r[2], r[2]) | |
| 9 | r[01] = MOD(r[2], r[3]) | |
| 10 | r[00] = ADD(r[1], r[0]) | |
| 11 | r[00] = ADD(r[0], r[0]) | |

In some embodiments, where r[00]≥0, a determination can be made that the subject would have a response (i.e., would be a responder) to a candidate treatment, and where r[00]<0, a determination can be made that the subject would not have a response (i.e., would be a non-responder) to the candidate treatment. For example, following the last operation above, the above model can further include a step including the instruction: if r[00]≥0, then the subject would have a response (i.e., would be a responder) to a candidate treatment; if r[00]<0, the subject would not have a response (i.e., would be a non-responder) to the candidate treatment.

The response value, r[00], compared to the threshold, 0, indicates a responsiveness of the subject to a candidate treatment by a predicted decrease in DAS28 score. As used in this model, "response" is defined as a decline in DAS28 of greater than 1.2 by 14 weeks after baseline.

Example 4

In order to validate the sets of markers, we obtained an additional data set of gene expression markers for rheumatoid arthritis patients using anti-TNF drugs as discussed in Julià A, Erra A, Palacio C, Tomas C, Sans X, et al. (2009) An Eight-Gene Blood Expression Profile Predicts the Response to Infliximab in Rheumatoid Arthritis. PLoS ONE 4(10): e7556. doi: 10.1371/journal.pone.0007556.

In Julià, microarray gene expression analysis was performed on whole blood RNA samples from RA patients starting infliximab therapy (n=44). The clinical response to infliximab was determined at week 14 using the EULAR criteria. Blood cell populations were determined using flow cytometry at baseline, week 2 and week 14 of treatment. Using complete cross-validation and repeated random sampling, an 8-gene predictor model was identified (96.6% Leave One Out prediction accuracy, P=0.0001). Applying this model to an independent validation set of RA patients, Julià estimated an 85.7% prediction accuracy (75-100%, 95% CI).

Whole-genome gene expression analysis was performed using the Illumina Human-6 v1 Beadchip array system (Illumina, San Diego, Calif., USA). This microarray platform measures the gene expression levels of more than 47,000 transcripts using 50-mer DNA probes fixed on a bead-based system. At the same time the microarray data was being acquired, an updated version of the Illumina Beadchip was launched. This new version included a redesign of several probe sequences, principally, those not belonging to the RefSeq database. The microarray analysis was restricted only on those probes that were still considered as valid (Illumina in-house data).

Only good quality blood RNAs (i.e. 28S/18S ratio close to 2, RNA Integrity Number 0.8) were subsequently processed using the Illumina gene expression assay. Biotin-labeled cRNA was hybridized to Sentrix whole genome beadchips and scanned on the Illumina BeadStation 500×. The raw intensity data was obtained from the scanned arrays using the BeadStudio software version 1.4.02 (Illumina, San Diego, Calif., USA), using the default probe summarization and background substraction methods. The statistical analyses were performed using the open-source statistical environment "R" and the associated Bioconductor project libraries for genomic analyses.

The log 2-transformed intensity values were normalized using the quantile normalization method implemented in the affy package. Quality control analysis of the normalized data identified an outlying gene expression profile which was excluded from further analyses. Before analyzing the normalized data, a filtering step was performed in order to exclude uninformative genes. Those probes for which all gene-expression values were under the lowest 5th percentile of the global gene expression values were considered as non-expressed and discarded (n=4,150). Probes with a low variability (coefficient of variation, 0.03, n=14,701) were also removed. All microarray data is in accordance with MIAME guidelines and is accessible through GEO database reference GSE12051.

The validation data set of Julià was analyzed using the same approach employed for the Merck data set, using only the final variables that emerged from the Merck analysis or a subset thereof (see Examples 1 and 2). Some of these variables were not available in the validation data sets. The HCMV marker was not available in the Julià data set. Of the three expression markers, only SEQ ID NO:3 was available in Julià. The Julià data set had no placebo subjects.

According to some embodiments, a model for determining whether a subject would have a response to a candidate treatment can include the following steps:

| Step Number | Instruction | Notation |
|---|---|---|
| 1 | r[01] = ADD(r[7], r[1]) | r[7] = SEQ ID NO: 3, r[1] = 5 |
| 2 | r[03] = MOD(r[1], r[3]) | r[3] = 2 |
| 3 | r[02] = DIV(r[7], r[3]) | r[7] = SEQ ID NO: 3 |
| 4 | r[01] = EXP(r[7]) | r[7] = SEQ ID NO: 3 |
| 5 | r[00] = MOD(r[1], r[2]) | |
| 6 | r[02] = SIN(r[0]) | |
| 7 | r[02] = SUB(r[1], r[2]) | |
| 8 | r[00] = MOD(r[1], r[2]) | |
| 9 | r[00] = SIN(r[0]) | |

In some embodiments, where r[00]≥0, a determination can be made that the subject would have a response (i.e., would be a responder) to a candidate treatment, and where r[00]<0, a determination can be made that the subject would not have a response (i.e., would be a non-responder) to the candidate treatment. For example, following the last operation above, the above model can further include a step including the instruction: if r[00]≥0, then the subject would have a response (i.e., would be a responder) to a candidate treatment; if r[00]<0, the subject would not have a response (i.e., would be a non-responder) to the candidate treatment.

The response value, r[00], compared to the threshold, 0, indicates a responsiveness of the subject to a candidate treatment by a predicted decrease in DAS28 score. As used in this model, "response" is defined as a decline in DAS28 of greater than 1.2 by 14 weeks after baseline.

Example 5

In order to validate the sets of markers, we obtained an additional data set of gene expression markers for rheumatoid arthritis patients using anti-TNF drugs as discussed in Bienkowska.

In Bienkowska, an analysis approach, the Convergent Random Forest (CRF) method, was evaluated by analyzing four different data sets. The first set contained transcript profiles of whole blood from rheumatoid arthritis patients, collected before anti-TNF treatment, and their subsequent response to the therapy. In this set, CRF identified 8 transcripts predicting response to therapy with 89% accuracy. Bienkowska also applied the CRF to the analysis of three previously published expression data sets. For all sets, Bienkowska compared the CRF and recursive support vector machines (RSVM) approaches to feature selection and classification.

Patient blood samples were collected pre-treatment in PAXgene tubes. Whole blood RNA was extracted and profiled using standard protocols on Affymetrix hgu133plus2 chips. Rheumatoid arthritis patients with active disease and naïve to TNF-blocking therapy were enlisted in the study. Response to TNF-blocking therapy was assessed after 14 weeks of treatment. Twenty-four patients were classified as responders and twenty-two as non-responders according to the EULAR classification. These data are available from the Gene Expression Omnibus (GEO) database at NCBI and has the accession number GSE15258.

Gene expression was analyzed starting with GCRMA normalization. Transcripts from the AbCoN training set was first reduced to those considered present in at least 50% in the samples from the same phenotypic group. Second, only transcripts that were significantly correlated with score for disease progression were selected. The significance was assessed using re-sampling and permutation. Third, only transcripts that were significantly different between responder, non-responder and healthy controls groups were considered. In the last and final step only transcripts with high expression and representing known genes in the ENTREZ database were selected. All analysis were done using the packages from R and Bioconductor.

The validation data set of Bienkowska was analyzed using the same approach employed for the Merck data set, using only the final variables that emerged from the Merck analysis or a subset thereof (see Examples 1 and 2). Some of these variables were not available in the validation data sets. The baseline DAS28 was available in Bienkowska. The HCMV marker was not available in the Bienkowska data set. Of the three expression markers, only SEQ ID NO:3 was available in Bienkowska. The Bienkowska data set had no placebo subjects According to some embodiments, a model for determining whether a subject would have a response to a candidate treatment can include the following steps:

| Step Number | Instruction | Notation |
|---|---|---|
| 1 | r[06] = MOD(r[12], r[5]) | r[12] = DAS28_0, r[5] = 7 |
| 2 | r[05] = SUB(r[10], r[1]) | r[10] = 29, r[1] = 1 |
| 3 | r[00] = POW(r[11], r[6]) | r[11] = 31 |
| 4 | r[00] = SIN(r[0]) | |
| 5 | r[07] = DIV(r[1], r[4]) | r[1] = 1, r[4] = 5 |
| 6 | r[03] = ADD(r[14], r[4]) | r[14] = SEQ ID NO: 3, r[4] = 5 |
| 7 | r[04] = ADD(r[0], r[7]) | |
| 8 | r[06] = MOD(r[5], r[0]) | |
| 9 | r[03] = POW(r[8], r[3]) | r[8] = 19 |
| 10 | r[01] = MOD(r[3], r[0]) | |
| 11 | r[00] = POW(r[11], r[6]) | r[11] = 31 |
| 12 | r[07] = DIV(r[1], r[4]) | |
| 13 | r[00] = SIN(r[0]) | |
| 14 | r[04] = ADD(r[0], r[7]) | |
| 15 | r[00] = DIV(r[10], r[4]) | r[10] = 29 |

In some embodiments, where r[00]≥0, a determination can be made that the subject would have a response (i.e., would be a responder) to a candidate treatment, and where r[00]<0, a determination can be made that the subject would not have a response (i.e., would be a non-responder) to the candidate treatment. For example, following the last operation above, the above model can further include a step including the instruction: if r[00]≥0, then the subject would have a response (i.e., would be a responder) to a candidate treatment; if r[00]<0, the subject would not have a response (i.e., would be a non-responder) to the candidate treatment.

The response value, r[00], compared to the threshold, 0, indicates a responsiveness of the subject to a candidate treatment by a predicted decrease in DAS28 score. As used in this model, "response" is defined as a decline in DAS28 of greater than 1.2 by 14 weeks after baseline.

Example 6

In order to produce a more generalized predictive algorithm, one data set or multiple data sets can be normalized and, if applicable, combined into a single data set. A predictive algorithm is then generated based on the normalized data set.

There are a variety of methods that may be used to normalize a data set, including but not limited to standard score, student's t-statistic, studentized residual, standardized moment, coefficient of variation, and feature scaling. For example, any normalization method that standardizes range or centrality can aid in producing a generalized algorithm. For the algorithms below, we can consider an unnamed first step in the algorithm to be a function labeled Norm(x), where x is the variable to be normalized, and Norm is the chosen normalizing operation. Therefore, the algorithms below can be considered to have a prefacing operation Norm(x) for every variable used in the algorithm. The normalized variables are then used as inputs, as shown.

The following algorithms were generated on a normalized data set. In some embodiments, the algorithms are generated on a single normalized data set. In other embodiments, the algorithms are created by normalizing two or more data sets in the same way, then combining the data sets into one data set.

According to some embodiments, a model for determining whether a subject would have a response to a candidate treatment can include the following steps:

| Step Number | Instruction | Notation |
|---|---|---|
| 1 | r[02] = ADD(r[5], r[2]) | r[5] = Norm(SEQ ID NO: 1), r[2] = 2 |

-continued

| Step Number | Instruction | Notation |
|---|---|---|
| 2 | r[00] = ADD(r[6], r[1]) | r[6] = Norm(SEQ ID NO: 2), r[1] = 1 |
| 3 | r[00] = DIV(r[2], r[0]) | |
| 4 | r[01] = SIN(r[6]) | r[6] = Norm(SEQ ID NO: 2) |
| 5 | r[00] = SUB(r[0], r[1]) | |
| 6 | r[02] = MOD(r[1], r[0]) | |
| 7 | r[03] = MOD(r[4], r[0]) | r[4] = 5 |
| 8 | r[00] = SIN(r[0]) | |
| 9 | r[00] = ADD(r[2], r[0]) | |
| 10 | r[03] = MUL(r[3], r[3]) | |
| 11 | r[02] = ADD(r[6], r[3]) | r[6] = Norm(SEQ ID NO: 2) |
| 12 | r[03] = DIV(r[3], r[2]) | |
| 13 | r[00] = ADD(r[3], r[0]) | |
| 14 | r[00] = ADD(r[3], r[0]) | |

According to some embodiments, a model for determining whether a subject would have a response to a candidate treatment can include the following steps:

| Step Number | Instruction | Notation |
|---|---|---|
| 1 | r[00] = SIN(r[1]) | r[1] = 1 |
| 2 | r[01] = SUB(r[1], r[0]) | r[1] = 1 |
| 3 | r[01] = SIN(r[1]) | |
| 4 | r[03] = SUB(r[6], r[1]) | r[6] = Norm(SEQ ID NO: 2) |
| 5 | r[03] = SIN(r[3]) | |
| 6 | r[02] = MOD(r[4], r[3]) | r[4] = 5 |
| 7 | r[00] = SIN(r[1]) | |
| 8 | r[00] = DIV(r[6], r[0]) | r[6] = Norm(SEQ ID NO: 2) |
| 9 | r[00] = MOD(r[0], r[1]) | |
| 10 | r[03] = MUL(r[3], r[0]) | |
| 11 | r[00] = SUB(r[7], r[3]) | r[7] = Norm(SEQ ID NO: 3) |
| 12 | r[03] = SUB(r[6], r[0]) | r[6] = Norm(SEQ ID NO: 2) |
| 13 | r[00] = SUB(r[7], r[3]) | r[7] = Norm(SEQ ID NO: 3) |
| 14 | r[00] = MOD(r[0], r[1]) | |
| 15 | r[00] = ADD(r[2], r[0]) | |

According to some embodiments, a model for determining whether a subject would have a response to a candidate treatment can include the following steps:

| Step Number | Instruction | Notation |
|---|---|---|
| 1 | r[07] = DIV(r[11], r[5]) | r[11] = 31, r[5] = 11 |
| 2 | r[04] = LN(r[13]) | r[13] = Norm(SEQ ID NO: 2) |
| 3 | r[00] = DIV(r[8], r[2]) | r[8] = 19, r[2] = 3 |
| 4 | r[01] = DIV(r[7], r[4]) | |
| 5 | r[07] = MOD(r[1], r[7]) | |
| 6 | r[04] = MOD(r[0], r[7]) | |
| 7 | r[00] = SUB(r[15], r[4]) | r[15] = Norm(SEQ ID NO: 3) |

According to some embodiments, a model for determining whether a subject would have a response to a candidate treatment can include the following steps:

| Step Number | Instruction | Notation |
|---|---|---|
| 1 | r[07] = LOGISTICFUNC(r[15]) | r[15] = Norm(SEQ ID NO: 3) |
| 2 | r[06] = DIV(r[11], r[3]) | r[11] = Treatment_num, r[3] = 5 |
| 3 | r[06] = SUB(r[13], r[6]) | r[13] = Norm(SEQ ID NO: 2) |
| 4 | r[01] = DIV(r[6], r[7]) | |
| 5 | r[05] = POW(r[15], r[7]) | r[15] = Norm(SEQ ID NO: 3) |
| 6 | r[00] = SUB(r[5], r[1]) | |

According to some embodiments, a model for determining whether a subject would have a response to a candidate treatment can include the following steps:

| Step Number | Instruction | Notation |
|---|---|---|
| 1 | r[02] = POW(r[7], r[2]) | r[7] = Norm(SEQ ID NO: 1), r[2] = Treatment_num |
| 2 | r[02] = MUL(r[6], r[2]) | r[6] = Norm(SEQ ID NO: 3) |
| 3 | r[02] = MUL(r[6], r[2] | r[6] = Norm(SEQ ID NO: 3) |
| 4 | r[02] = MUL(r[6], r[2]) | r[6] = Norm(SEQ ID NO: 3) |
| 5 | r[02] = SUB(r[4], r[2]) | r[4] = Norm(SEQ ID NO: 2) |
| 6 | r[02] = POW(r[6], r[2]) | r[6] = Norm(SEQ ID NO: 3) |
| 7 | r[03] = MUL(r[3], r[0]) | r[3] = Norm(SEQ ID NO: 2), r[0] = Treatment_num |
| 8 | r[03] = POW(r[3], r[0]) | r[0] = Treatment_num |
| 9 | r[00] = SUB(r[5], r[3]) | r[5] = Norm(SEQ ID NO: 3) |
| 10 | r[03] = MUL(r[5], r[3]) | r[5] = Norm(SEQ ID NO: 3) |
| 11 | r[01] = SUB(r[2], r[3]) | |
| 12 | r[00] = ADD(r[0], r[0]) | |
| 13 | r[00] = ADD(r[7], r[0]) | r[7] = Norm(SEQ ID NO: 1) |
| 14 | r[01] = ADD(r[1], r[0]) | |
| 15 | r[00] = DIV(r[5], r[0]) | r[5] = Norm(SEQ ID NO: 3) |
| 16 | r[00] = ADD(r[1], r[0]) | |
| 17 | r[01] = DIV(r[4], r[1]) | r[4] = Norm(SEQ ID NO: 2) |
| 18 | r[00] = ADD(r[0], r[0]) | |
| 19 | r[00] = ADD(r[0], r[0]) | |
| 20 | r[00] = ADD(r[1], r[0]) | |

According to some embodiments, a model for determining whether a subject would have a response to a candidate treatment can include the following steps:

| Step Number | Instruction | Notation |
|---|---|---|
| 1 | r[06] = MUL(r[12], r[1]) | r[12] = Treatment_num, r[1] = 2 |
| 2 | r[07] = MUL(r[14], r[4]) | r[14] = Norm(SEQ ID NO: 1), r[4] = 7 |
| 3 | r[07] = SUB(r[5], r[7]) | r[5] = 11 |
| 4 | r[06] = SUB(r[6], r[7]) | |
| 5 | r[00] = DIV(r[3], r[6]) | r[3] = 5 |
| 6 | r[05] = SUB(r[14], r[7]) | r[14] = Norm(SEQ ID NO: 1) |
| 7 | r[02] = DIV(r[13], r[5]) | r[13] = Norm(SEQ ID NO: 2) |
| 8 | r[07] = SUB(r[13], r[7]) | r[13] = Norm(SEQ ID NO: 2) |
| 9 | r[00] = ADD(r[2], r[0]) | |
| 10 | r[05] = SUB(r[14], r[7]) | r[14] = Norm(SEQ ID NO: 1) |
| 11 | r[02] = DIV(r[1], r[5]) | r[1] = 2 |
| 12 | r[00] = ADD(r[2], r[0]) | |

According to some embodiments, a model for determining whether a subject would have a response to a candidate treatment can include the following steps:

| Step Number | Instruction | Notation |
|---|---|---|
| 1 | r[01] = DIV(r[8], r[1]) | r[8] = 19, r[1] = 2 |
| 2 | r[05] = DIV(r[15], r[1]) | r[15] = Norm(SEQ ID NO: 3) |
| 3 | r[00] = SUB(r[13], r[6]) | r[13] = Norm(SEQ ID NO: 2), r[6] = 13 |
| 4 | r[07] = DIV(r[6], r[0]) | r[6] = 13 |
| 5 | r[04] = DIV(r[12], r[6]) | r[12] = Treatment_num, r[6] = 13 |
| 6 | r[05] = SUB(r[14], r[5]) | r[14] = Norm(SEQ ID NO: 1) |
| 7 | r[07] = ADD(r[7], r[5]) | |
| 8 | r[05] = SUB(r[4], r[7]) | |
| 9 | r[00] = DIV(r[5], r[7]) | |
| 10 | r[07] = MUL(r[0], r[7]) | |
| 11 | r[07] = MUL(r[0], r[7]) | |
| 12 | r[00] = ADD(r[0], r[0]) | |
| 13 | r[00] = ADD(r[15], r[0]) | r[15] = Norm(SEQ ID NO: 3) |
| 14 | r[00] = ADD(r[7], r[0]) | |

According to some embodiments, a model for determining whether a subject would have a response to a candidate treatment can include the following steps:

| | | |
|---|---|---|
| 1 | r[03] = DIV(r[6], r[3]) | r[6] = Norm(SEQ ID NO: 1), r[3] = 5 |
| 2 | r[02] = MOD(r[0], r[3]) | r[0] = 7 |
| 3 | r[01] = ADD(r[3], r[2]) | |
| 4 | r[03] = SUB(r[6], r[2]) | r[6] = Norm(SEQ ID NO: 1) |
| 5 | r[02] = POW(r[6], r[1]) | r[6] = Norm(SEQ ID NO: 1) |
| 6 | r[03] = ADD(r[5], r[3]) | r[5] = Norm(SEQ ID NO: 2) |
| 7 | r[00] = MOD(r[3], r[2]) | |
| 8 | r[00] = SUB(r[1], r[0]) | |

In some embodiments, where r[00]≥0, a determination can be made that the subject would have a response (i.e., would be a responder) to a candidate treatment, and where r[00]<0, a determination can be made that the subject would not have a response (i.e., would be a non-responder) to the candidate treatment. For example, following the last operation above, any one of the above models can further include a step including the instruction: if r[00]≥0, then the subject would have a response (i.e., would be a responder) to a candidate treatment; if r[00]<0, the subject would not have a response (i.e., would be a non-responder) to the candidate treatment. In some embodiments, the response value, r[00], compared to the threshold, 0, indicates a responsiveness of the subject to a candidate treatment by a predicted decrease in DAS28 score. As used in any of the above models, in some implementations, "response" is defined as a decline in DAS28 of greater than 1.2 by 14 weeks after baseline.

In other embodiments, where r[00] is a number between the mean of sample subject(s) who respond to an anti-TNF treatment and the mean of sample subject(s) who do not response an anti-TNF treatment, a determination can be made that the subject would have a response (i.e., would be a responder) to a candidate treatment. For example, given a data set, the responsiveness of the sample subjects to an anti-TNF treatment is known. Using any of the above model, r[00] for each sample subject in the data set may be calculated. r[00]'—mean of r[00] for sample subject(s) who respond to an anti-TNF treatment—may be calculated. Likewise, r[00]"—mean of r[00] for sample subject(s) who do not respond to an anti-TNF treatment—may be calculated. For the subject whose responsiveness to an anti-TNF treatment is to be determined, if r[00] of the subject is a number between r[00]' and r[00]", a determination can be made that the subject would have a response (i.e., would be a responder) to a candidate treatment. By way of example, if r[00]' is 0.5, and r[00]" is −0.6, then the threshold may be any number between −0.6 and 0.5. The threshold may be −0.3. If [r00] for the subject is −0.1, then the subject can be predicted to response to an anti-TNF treatment.

In some embodiments, beyond a threshold refers to move from the threshold towards the mean of the response values of sample subjects who respond to an anti-TNF treatment. Using the above example, −0.1 is beyond the threshold of −0.3, as −0.1 moves from −0.3 towards 0.5.

In some embodiments, where r[00] is beyond a threshold, a determination can be made that the subject would have a response (i.e., would be a responder) to a candidate treatment, and where r[00] is not beyond the threshold, a determination can be made that the subject would not have a response (i.e., would be a non-responder) to the candidate treatment. For example, following the last operation above, any one of the above models can further include a step including the instruction: if r[00] is beyond a threshold, then the subject would have a response (i.e., would be a responder) to a candidate treatment; if r[00] is not beyond the threshold, the subject would not have a response (i.e., would be a non-responder) to the candidate treatment.

Treatment

According to some embodiments, an antagonist is administered at a frequency of one to four doses within a period of about one month. The antagonist can be administered in two to three doses. In addition, the antagonist can be administered within a period of about 2 to 3 weeks.

According to some embodiments, the anti-TNF is administered without any other medicament to treat the RA. According to some embodiments, the method further comprises administering an effective amount of one or more second medicaments with the anti-TNF, wherein the anti-TNF is a first medicament. According to some embodiments, the medicament is optionally selected from the group consisting of anti-alpha4, etanercept, infliximab, adalimumab, kinaret, efalizumab, osteoprotegerin (OPG), anti-receptor activator of NFKB ligand (anti-RANKL), anti-receptor activator of NFKB-FC (RANK-FC), pamidronate, alendronate, actonel, zolendronate, clodronate, MTX, azulfidine, hydroxychloroquine, doxycycline, leflunomide, SSZ, prednisolone, interleukin-1 receptor antagonist, prednisone, and methylprednisolone.

According to some embodiments, at least about three months after the commencement of administration, an imaging test (radiographic and/or MRI) is given that measures a reduction in bone and soft tissue joint damage as compared to baseline prior to the administration, and the amount of antagonist administered is effective in achieving a reduction in the joint damage.

Systems

Figure 5:
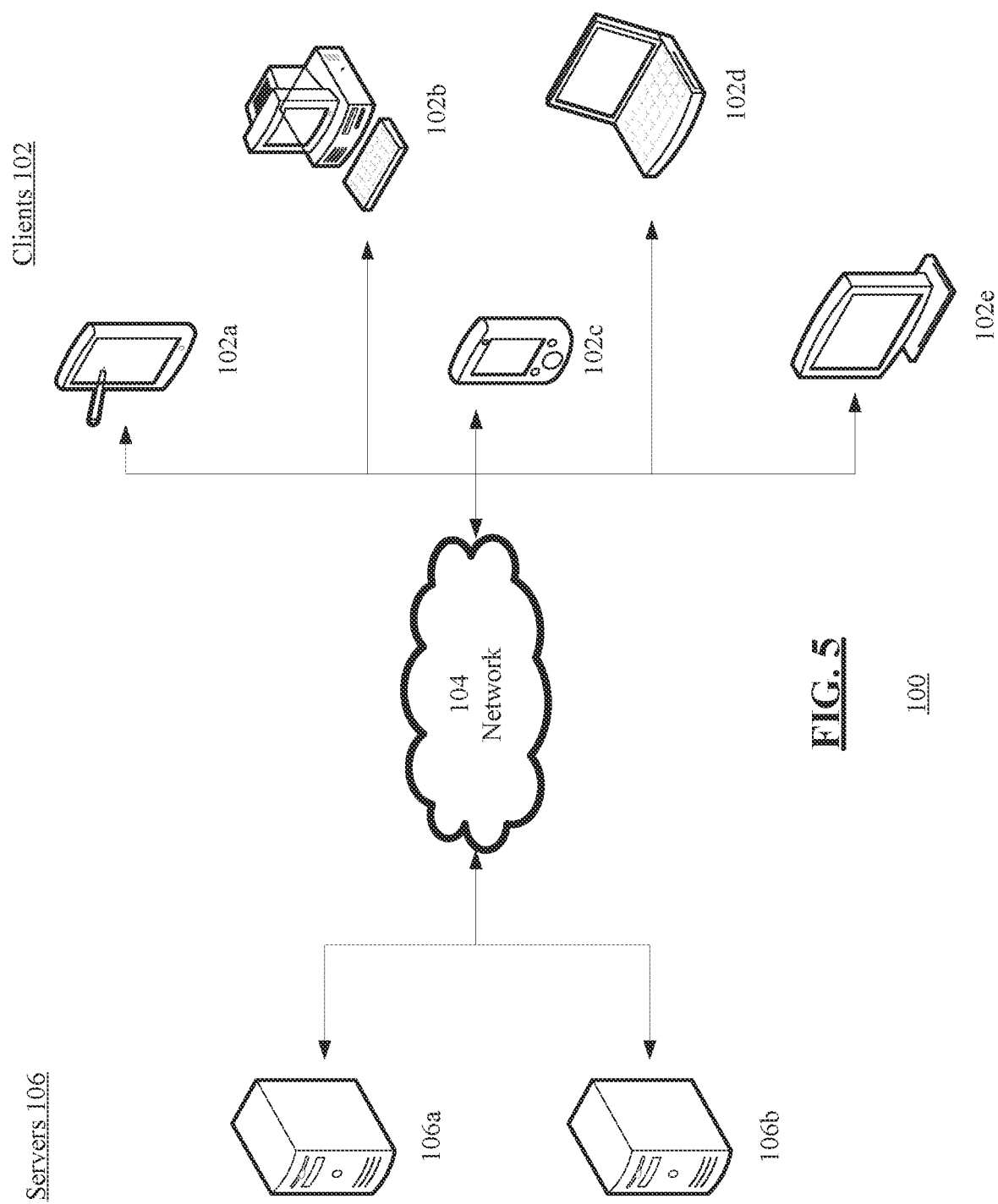
FIG. 5 is an exemplary diagram of a network in which systems and methods herein may be implemented.

FIG. 5 is a simplified diagram of a system 100, in accordance with various embodiments of the subject technology. The system 100 may include one or more remote client devices 102 (e.g., client devices 102a, 102b, 102c, 102d, and 102e) in communication with one or more server computing devices 106 (e.g., servers 106a and 106b) via network 104. In some embodiments, a client device 102 is configured to run one or more applications based on communications with a server 106 over a network 104. In some embodiments, a server 106 is configured to run one or more applications based on communications with a client device 102 over the network 104. In some embodiments, a server 106 is configured to run one or more applications that may be accessed and controlled at a client device 102. For example, a user at a client device 102 may use a web browser to access and control an application running on a server 106 over the network 104. In some embodiments, a server 106 is configured to allow remote sessions (e.g., remote desktop sessions) wherein users can access applications and files on a server 106 by logging onto a server 106 from a client device 102. Such a connection may be established using any of several well-known techniques such as the Remote Desktop Protocol (RDP) on a Windows-based server.

By way of illustration and not limitation, in some embodiments, stated from a perspective of a server side (treating a server as a local device and treating a client device as a remote device), a server application is executed (or runs) at a server 106. While a remote client device 102 may receive and display a view of the server application on a display local to the remote client device 102, the remote client device 102 does not execute (or run) the server application at the remote client device 102. Stated in another way from a perspective of the client side (treating a server as remote device and treating a client device as a local device), a remote application is executed (or runs) at a remote server 106.

By way of illustration and not limitation, in some embodiments, a client device 102 can represent a desktop computer, a mobile phone, a laptop computer, a netbook computer, a tablet, a thin client device, a personal digital assistant (PDA), a portable computing device, and/or a suitable device with a processor. In one example, a client device 102 is a smartphone (e.g., iPhone, Android phone, Blackberry, etc.). In certain configurations, a client device 102 can represent an audio player, a game console, a camera, a camcorder, a Global Positioning System (GPS) receiver, a television set top box an audio device, a video device, a multimedia device, and/or a device capable of supporting a connection to a remote server. In some embodiments, a client device 102 can be mobile. In some embodiments, a client device 102 can be stationary. According to certain embodiments, a client device 102 may be a device having at least a processor and memory, where the total amount of memory of the client device 102 could be less than the total amount of memory in a server 106. In some embodiments, a client device 102 does not have a hard disk. In some embodiments, a client device 102 has a display smaller than a display supported by a server 106. In some aspects, a client device 102 may include one or more client devices.

In some embodiments, a server 106 may represent a computer, a laptop computer, a computing device, a virtual machine (e.g., VMware® Virtual Machine), a desktop session (e.g., Microsoft Terminal Server), a published application (e.g., Microsoft Terminal Server), and/or a suitable device with a processor. In some embodiments, a server 106 can be stationary. In some embodiments, a server 106 can be mobile. In certain configurations, a server 106 may be any device that can represent a client device. In some embodiments, a server 106 may include one or more servers.

In some embodiments, a first device is remote to a second device when the first device is not directly connected to the second device. In some embodiments, a first remote device may be connected to a second device over a communication network such as a Local Area Network (LAN), a Wide Area Network (WAN), and/or other network.

When a client device 102 and a server 106 are remote with respect to each other, a client device 102 may connect to a server 106 over the network 104, for example, via a modem connection, a LAN connection including the Ethernet or a broadband WAN connection including DSL, Cable, T1, T3, Fiber Optics, Wi-Fi, and/or a mobile network connection including GSM, GPRS, 3G, 4G, 4G LTE, WiMax or other network connection. Network 104 can be a LAN network, a WAN network, a wireless network, the Internet, an intranet, and/or other network. The network 104 may include one or more routers for routing data between client devices and/or servers. A remote device (e.g., client device, server) on a network may be addressed by a corresponding network address, such as, but not limited to, an Internet protocol (IP) address, an Internet name, a Windows Internet name service (WINS) name, a domain name, and/or other system name. These illustrate some examples as to how one device may be remote to another device, but the subject technology is not limited to these examples.

According to certain embodiments of the subject technology, the terms "server" and "remote server" are generally used synonymously in relation to a client device, and the word "remote" may indicate that a server is in communication with other device(s), for example, over a network connection(s).

According to certain embodiments of the subject technology, the terms "client device" and "remote client device" are generally used synonymously in relation to a server, and the word "remote" may indicate that a client device is in communication with a server(s), for example, over a network connection(s).

In some embodiments, a "client device" may be sometimes referred to as a client or vice versa. Similarly, a "server" may be sometimes referred to as a server device or server computer or like terms.

In some embodiments, the terms "local" and "remote" are relative terms, and a client device may be referred to as a local client device or a remote client device, depending on whether a client device is described from a client side or from a server side, respectively. Similarly, a server may be referred to as a local server or a remote server, depending on whether a server is described from a server side or from a client side, respectively. Furthermore, an application running on a server may be referred to as a local application, if described from a server side, and may be referred to as a remote application, if described from a client side.

In some embodiments, devices placed on a client side (e.g., devices connected directly to a client device(s) or to one another using wires or wirelessly) may be referred to as local devices with respect to a client device and remote devices with respect to a server. Similarly, devices placed on a server side (e.g., devices connected directly to a server(s) or to one another using wires or wirelessly) may be referred to as local devices with respect to a server and remote devices with respect to a client device.

Figure 6:
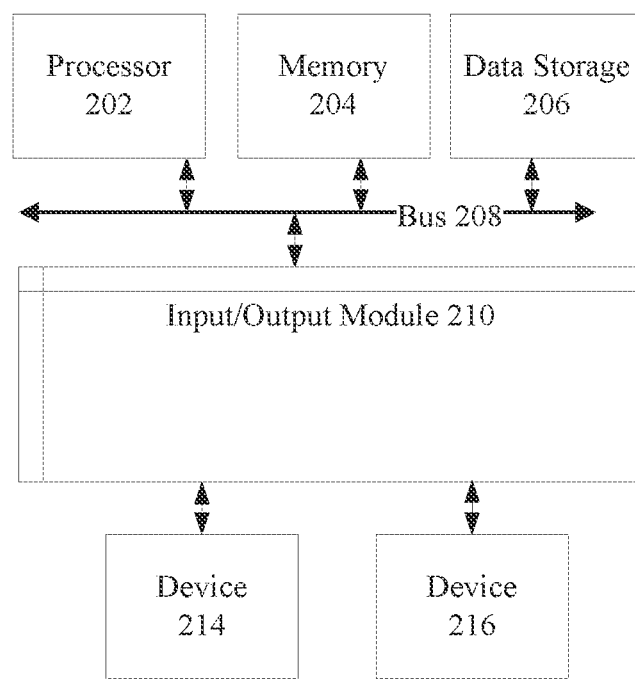
FIG. 6 is an exemplary diagram of a client or server of FIG. 5.

FIG. 6 is a block diagram illustrating an exemplary computer system 200 with which a client device 102 and/or a server 106 of FIG. 5 can be implemented. In certain embodiments, the computer system 200 may be implemented using hardware or a combination of software and hardware, either in a dedicated server, or integrated into another entity, or distributed across multiple entities.

The computer system 200 (e.g., client 102 and servers 106) includes a bus 208 or other communication mechanism for communicating information, and a processor 202 coupled with the bus 208 for processing information. By way of example, the computer system 200 may be implemented with one or more processors 202. The processor 202 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, and/or any other suitable entity that can perform calculations or other manipulations of information.

The computer system 200 can include, in addition to hardware, code that creates an execution environment for the computer program in question, e.g., code that constitutes processor firmware, a protocol stack, a database management system, an operating system, or a combination of one or more of them stored in an included memory 204, such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, and/or any other suitable storage device, coupled to the bus 208 for storing information and instructions to be executed by the processor 202. The processor 202 and the memory 204 can be supplemented by, or incorporated in, special purpose logic circuitry.

The instructions may be stored in the memory 204 and implemented in one or more computer program products, i.e., one or more modules of computer program instructions encoded on a computer readable medium for execution by, or to control the operation of, the computer system 200, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and/or application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, and/or xml-based languages. The memory 204 may also be used for storing temporary variable or other intermediate information during execution of instructions to be executed by the processor 202.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

The computer system 200 further includes a data storage device 206 such as a magnetic disk or optical disk, coupled to the bus 208 for storing information and instructions. The computer system 200 may be coupled via an input/output module 210 to various devices (e.g., devices 214 and 216). The input/output module 210 can be any input/output module. Exemplary input/output modules 210 include data ports (e.g., USB ports), audio ports, and/or video ports. In some embodiments, the input/output module 210 includes a communications module. Exemplary communications modules include networking interface cards, such as Ethernet cards, modems, and routers. In certain aspects, the input/output module 210 is configured to connect to a plurality of devices, such as an input device 214 and/or an output device 216. Exemplary input devices 214 include a keyboard and/or a pointing device (e.g., a mouse or a trackball) by which a user can provide input to the computer system 200. Other kinds of input devices 214 can be used to provide for interaction with a user as well, such as a tactile input device, visual input device, audio input device, and/or brain-computer interface device. For example, feedback provided to the user can be any form of sensory feedback (e.g., visual feedback, auditory feedback, and/or tactile feedback), and input from the user can be received in any form, including acoustic, speech, tactile, and/or brain wave input. Exemplary output devices 216 include display devices, such as a cathode ray tube (CRT) or liquid crystal display (LCD) monitor, for displaying information to the user.

According to certain embodiments, a client device 102 and/or server 106 can be implemented using the computer system 200 in response to the processor 202 executing one or more sequences of one or more instructions contained in the memory 204. Such instructions may be read into the memory 204 from another machine-readable medium, such as the data storage device 206. Execution of the sequences of instructions contained in the memory 204 causes the processor 202 to perform the process steps described herein. One or more processors in a multi-processing arrangement may also be employed to execute the sequences of instructions contained in the memory 204. In some embodiments, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component (e.g., a data server), or that includes a middleware component (e.g., an application server), or that includes a front end component (e.g., a client computer having a graphical user interface and/or a Web browser through which a user can interact with an implementation of the subject matter described in this specification), or any combination of one or more such back end, middleware, or front end components. The components of the system 200 can be interconnected by any form or medium of digital data communication (e.g., a communication network). Examples of communication networks include a local area network and a wide area network.

The term "machine-readable storage medium" or "computer readable medium" as used herein refers to any medium or media that participates in providing instructions to the processor 202 for execution. Such a medium may take many forms, including, but not limited to, non-volatile media, volatile media, and transmission media. Non-volatile media include, for example, optical or magnetic disks, such as the data storage device 206. Volatile media include dynamic memory, such as the memory 204. Transmission media include coaxial cables, copper wire, and fiber optics, including the wires that comprise the bus 208. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

As used herein, a "processor" can include one or more processors, and a "module" can include one or more modules.

In an aspect of the subject technology, a machine-readable medium is a computer-readable medium encoded or stored with instructions and is a computing element, which defines structural and functional relationships between the instructions and the rest of the system, which permit the instructions' functionality to be realized. Instructions may be executable, for example, by a system or by a processor of the system. Instructions can be, for example, a computer program including code. A machine-readable medium may comprise one or more media.

Figure 7:
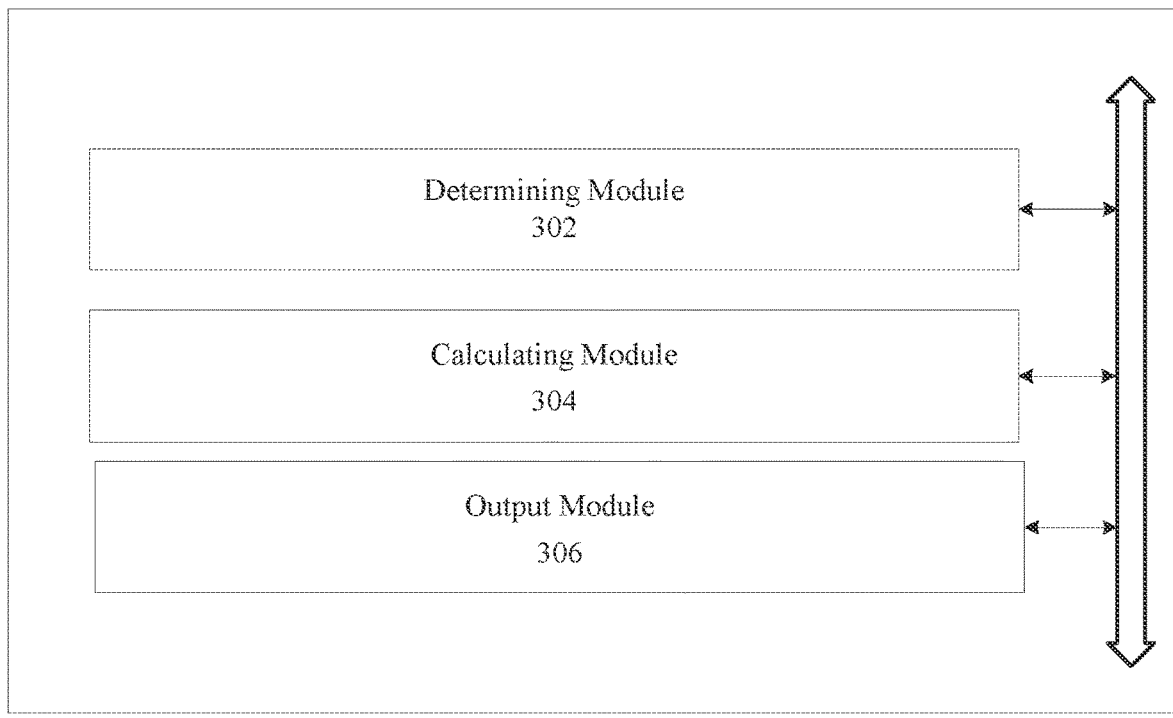
FIG. 7 is an exemplary diagram of modules implementing methods of the subject technology.

FIG. 7 illustrates an example of a system 300 for predicting response to a medicament, in accordance with various embodiments of the subject technology. The system 300 is an example of an implementation of a client device 102 and/or a server 106 for predicting response to a medicament. The system 300 comprises determining module 302, calculating module 304, and output module 306. Although the system 300 is shown as having these modules, the system 300 may have other suitable configurations. The modules of the system 300 may be in communication with one another. In some embodiments, the modules may be implemented in software (e.g., subroutines and code). For example, the modules may be stored in the memory 204 and/or data storage 206, and executed by the processor 202. In some aspects, some or all of the modules may be implemented in hardware (e.g., an Application Specific Integrated Circuit (ASIC), a Field Programmable Gate Array (FPGA), a Programmable Logic Device (PLD), a controller, a state machine, gated logic, discrete hardware components, or any other suitable devices) and/or a combination of both. Additional features and functions of these modules according to various aspects of the subject technology are further described in the present disclosure.

As used herein, the word "module" refers to logic embodied in hardware or firmware, or to a collection of software instructions, possibly having entry and exit points, written in a programming language, such as, for example C++. A software module may be compiled and linked into an executable program, installed in a dynamic link library, or may be written in an interpretive language such as BASIC. It will be appreciated that software modules may be callable from other modules or from themselves, and/or may be invoked in response to detected events or interrupts. Software instructions may be embedded in firmware, such as an EPROM or EEPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware.

It is contemplated that the modules may be integrated into a fewer number of modules. One module may also be separated into multiple modules. The described modules may be implemented as hardware, software, firmware or any combination thereof. Additionally, the described modules may reside at different locations connected through a wired or wireless network, or the Internet.

In general, it will be appreciated that the processors can include, by way of example, computers, program logic, or other substrate configurations representing data and instructions, which operate as described herein. In other embodiments, the processors can include controller circuitry, processor circuitry, processors, general purpose single-chip or multi-chip microprocessors, digital signal processors, embedded microprocessors, microcontrollers and the like.

Furthermore, it will be appreciated that in one embodiment, the program logic may advantageously be implemented as one or more components. The components may advantageously be configured to execute on one or more processors. The components include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A method of treatment, comprising:
(a) measuring, from a sample of a subject prior to administration of a TNF inhibitor treatment to the subject, (b) an amount of an mRNA sequence corresponding to SEQ ID NO: 2, present in the sample; and (c) an amount of an mRNA sequence comprising SEQ ID NO: 3, present in the sample;
identifying a subject as a responsive subject when the subject, prior to administration of the TNF inhibitor treatment, has a response value substantially equivalent to the final r[00] calculated in the sequence of operations below and beyond a threshold:
1 r[00]=SIN r[1])
2 r[01]=SUB(r[1],r[0])
3 r[01]=SIN(r[1])
4 r[03]=SUB(r[6],r[1])
5 r[03]=SIN(r[3])
6 r[02]=MOD(r[4], r[3])
7 r[00]=SIN(r[1])
8 r[00]=DIV(r[6], r[0])
9 r[00]=MOD(r[0], r[1])
10 r[03]=MUL(r[3], rj0j)
11 r[00]=SUB(r[7], r[3])
12 r[03]=SUB (r[6], r[0])
13 r[00]=SUB(r[7], r[3])
14 r[00]=MOD(r[0], r[1])
15 r[00]=ADD(r[2], r[0])
wherein:
r[1]=1
r[6] is a normalized value of the amount of the mRNA sequence corresponding to SEQ ID NO: 2; and
r[7] is a normalized value of the amount of the mRNA sequence corresponding to SEQ ID NO: 3; and
after identifying a responsive subject, treating the responsive subject by administering an effective amount of a medicament comprising a TNF inhibitor.

2. The method of claim 1, wherein after the administering, the responsive subject has a decrease in a DAS28 score.

3. The method of claim 1, further comprising: not administering the medicament to the subject, within one month of the diagnosing, when the response value is not beyond the threshold.

4. The method of claim 1, wherein the medicament comprises infliximab, adalimumab, leflunomide, anakinra, azathioprine, cyclophosphamide, and/or etanercept.

5. The method of claim 1, wherein the medicament comprises an anti-inflammatory agent and/or a monoclonal antibody.

6. The method of claim 1, wherein the responsive subject has a decrease in DAS28 score within a 14 week period after administering the medicament.

7. The method of claim 1, wherein the responsive subject has a decrease in DAS28 score by 1.2 or more within a 14 week period after commencing administering the medicament.

8. The method of claim 1, wherein the threshold is 0 or a value between a first value and a second value, wherein the first value is a mean of sample response values of a first one or more sample subjects who respond to an anti-TNF treatment, and the second value is a mean of sample response values of a second one or more subjects who do not respond to
the anti-TNF treatment, and wherein the sample response values for each of the sample subjects is determined based on the amount of an mRNA sequence corresponding to SEQ ID NO: 1, present in the sample; and the amount of an mRNA sequence comprising SEQ ID NO:2, present in the sample.

9. A method of treatment, comprising:
(a) measuring, from a sample of a subject prior to administration of a TNF inhibitor treatment to the subject, (b) an amount of an mRNA sequence corresponding to SEQ ID NO: 2, present in the sample; and (c) an amount of an mRNA sequence comprising SEQ ID NO: 3, present in the sample;
identifying a responsive subject when the subject, prior to administration of the TNF inhibitor treatment, has a response value substantially equivalent to the final r[00] calculated in the sequence of operations below and beyond a threshold:
1 r[07]=DIV(31, 11)
2 r[04]=LN(r[13])
3 r[00]=DIV(19, 3)
4 r[01]=DIV(r[7], r[4])
5 r[07]=MOD(r[I], r[7])
6 r[04]=MOD(r[0], r[7])
7 r[00]=SUB(r[15], r[4])
wherein:
r[13] is a normalized value of the amount of the mRNA sequence corresponding to SEQ ID NO:2;

r[15] is a normalized value of the amount of the mRNA sequence corresponding to SEQ ID NO:3; and after identifying a responsive subject, treating the responsive subject by administering an effective amount of a medicament comprising a TNF inhibitor.

10. The method of claim 9, wherein after the administering, the responsive subject has a decrease in a DAS28 score.

11. The method of claim 9, further comprising: not administering the medicament to the subject, within one month of the diagnosing, when the response value is not beyond the threshold.

12. The method of claim 9, wherein the medicament comprises infliximab, adalimumab, leflunomide, anakinra, azathioprine, cyclophosphamide, and/or etanercept.

13. The method of claim 9, wherein the medicament comprises an anti-inflammatory agent and/or a monoclonal antibody.

14. The method of claim 9, wherein the responsive subject has a decrease in DAS28 score within a 14 week period after administering the medicament.

15. The method of claim 9, wherein the responsive subject has a decrease in DAS28 score by 1.2 or more within a 14 week period after commencing administering the medicament.

16. The method of claim 9, wherein the threshold is 0 or a value between a first value and a second value, wherein the first value is a mean of sample response values of a first one or more sample subjects who respond to an anti-TNF treatment, and the second value is a mean of sample response values of a second one or more subjects who do not respond to the anti-TNF treatment, and wherein the sample response values for each of the sample subjects is determined based on the amount of an mRNA sequence corresponding to SEQ ID NO: 1, present in the sample; and the amount of an mRNA sequence comprising SEQ ID NO: 2, present in the sample.

17. A method of treatment, comprising:
measuring, from a sample of a subject prior to administration of a TNF inhibitor treatment to the subject, (b) an amount of an mRNA sequence corresponding to SEQ ID NO: 2, present in the sample; and (c) an amount of an mRNA sequence comprising SEQ ID NO: 3, present in the sample;

identifying a responsive subject as a responsive subject when the subject, prior to administration of the TNF inhibitor treatment, has a response value substantially equivalent to the final r[00]
calculated in the sequence of operations below and beyond a threshold:
1 r[07]=LOGISTICFUNC(r[15])
2 r[06]=DIV(r[11], 5)
3 r[06]=SUB(r[13], r[6])
4 r[01]=DIV(r[6], r[7])
5 r[05]=POW(r[15], r[7])
6 r[00]=SUB(r[5], r[1])

wherein:
r[15] is a normalized value of the amount of the mRNA sequence corresponding to SEQ ID NO: 3;
r[11]=Treatment_num, wherein Treatment_num=1 if the subject is administered a
drug, Treatment_num=0 if the subject is administered a placebo;
r[13] is a normalized value of the amount of the mRNA sequence corresponding to SEQ ID NO:2; and after identifying a responsive subject, treating the responsive subject by administering an effective amount of a medicament comprising a TNF inhibitor.

18. The method of claim 17, wherein after the administering, the responsive subject has a decrease in a DAS28 score.

19. The method of claim 17, further comprising: not administering the medicament to the subject, within one month of the diagnosing, when the response value is not beyond the threshold.

20. The method of claim 17, wherein the medicament comprises infliximab, adalimumab, leflunomide, anakinra, azathioprine, cyclophosphamide, and/or etanercept.

21. The method of claim 17, wherein the medicament comprises an anti-inflammatory agent and/or a monoclonal antibody.

22. The method of claim 17, wherein the responsive subject has a decrease in DAS28 score within a 14 week period after administering the medicament.

23. The method of claim 17, wherein the responsive subject has a decrease in DAS28 score by 1.2 or more within a 14 week period after commencing administering the medicament.

24. The method of claim 17, wherein the threshold is 0 or a value between a first value and a second value, wherein the first value is a mean of sample response values of a first one or more sample subjects who respond to an anti-TNF treatment, and the second value is a mean of sample response values of a second one or more subjects who do not respond to the anti-TNF treatment, and wherein the sample response values for each of the sample subjects is determined based on the amount of an mRNA sequence corresponding to SEQ ID NO: 1, present in the sample; and the amount of an mRNA sequence comprising SEQ ID NO: 2, present in the sample.

25. The method of claim 1, further comprising a step of measuring one or more of:
an amount of an mRNA sequence corresponding to SEQ ID NO: 1 present in the sample;
an amount of an mRNA sequence corresponding to SEQ ID NO: 4 present in the sample; and
an amount of an mRNA sequence corresponding to SEQ ID NO: 5 present in the sample.

* * * * *

SEQUENCE LISTING

```
<160> NUMBER OF SEQ ID NOS: 5

<210> SEQ ID NO 1
<211> LENGTH: 344
<212> TYPE: DNA
<213> ORGANISM: Homo sapiens

<400> SEQUENCE: 1
gaagctcctt agtgaggagc tgccatgctg ggccatccac catctggatt cctacgactc      60
agggaataga acactgcacc ttccagaagc acttgtttct tcgtgggtac accaccagct     120
gagaaagaag cctcatgatg attgttgtct tatggatgct tctcattgca ggaaccatgt     180
ggaagggata taaatatccc ccaggaggga ctccagtgga agtaagcaag gatgatcctg     240
gtgaagtaat gcagctgtga agctcacctg accagctgta cagttcctgt tgttggtttc     300
acataaagta attgcacatt attttgtcat aaaaaaaaaa aaaa                      344

<210> SEQ ID NO 2
<211> LENGTH: 985
<212> TYPE: DNA
<213> ORGANISM: Homo sapiens

<400> SEQUENCE: 2
atgtaaatca cacagatgtt ggtagagaaa aaggcatact ggtattgaaa ctgtaaactg      60
gcctgtttac ttcgtctcct aacaaaaaac actttggatt caggttctcc acagcagtct     120
tccactggcc acagtgaggg gagctaggtt tccccagtct ccagctagaa aaactcagaa     180
catctaaaga tctgaaagat ggaaaaaaga gaactaaagg cttctgttcc aaaatttgac     240
aagattcctt ggcttagtga ggccagcctt gtaaacaagc cattagtgct cagccttccc     300
agaagatatc ctcatacctc tgcgactttt ctgacttcat ccaagaagaa tatgaatttg     360
ccaattttgt ttcaagttcc agatgtttta tctaaggcca ggaggaacca gtgtgactcc     420
atgctgctca gaaaccaaca gctgtgctcc acatgtcaag aaatgaaaat ggtacaacca     480
agaacaatga aaatcccaga tgatccaaaa gcatcctttg agaattgtat gagttataga     540
atgagtcttc atcaacccaa attccagact acacctgagc ctttccatga tgacatccca     600
acagaaagca ttcactacag actgcccatt ctgggcccca ggacagctgt cttccacgga     660
ttactgacag aggcctacaa aactctaaaa gagagacaac gttcttcctt gcccagaaag     720
gaaccaatag gcaagacaac gaggcagtga gcggtaggag ctcatcacct cccagactcc     780
cagagagaaa ataacctcgc caagccaatc tttgacactg gcaccttctc ctcacaattt     840
tctctcttct cccaaaagat gatttaattt tgccttccta agattgctgg tattctagct     900
```

```
cttacctcta tgttctttct cacgtctcct aaagacaaaa ttgtttaatt tacatgatta    960
taaagatctg tttatgaaaa tggaa                                          985
```

<210> SEQ ID NO 3
<211> LENGTH: 722
<212> TYPE: DNA
<213> ORGANISM: Homo sapiens
<220> FEATURE:
<221> NAME/KEY: modified_base
<222> LOCATION: (683)..(683)
<223> OTHER INFORMATION: a, c, t, g, unknown or other
<220> FEATURE:
<221> NAME/KEY: modified_base
<222> LOCATION: (702)..(702)
<223> OTHER INFORMATION: a, c, t, g, unknown or other

<400> SEQUENCE: 3

```
tttttttttt ttttttttag caaaagcttt cagtctttat ttacagtata tagaaggtta     60
ctgttttcat tttaggtgga agagtctgat cagtaggaac accccagagg aaggacatct    120
ttagcgatag aatttacata ccgttagctc acagtaattg attagtagca gggctctgta    180
gtacagagct agctgggcat gttatttggg atgtctttga tgctgtggtt ttccgaagct    240
tgctggctgc atgcttgttg cctttgttcg tgacacaggg aattacttga taaatgaag    300 tgcatcgctg tgaacaattg acccttggaa caatccagg ctggtcagca gtctaaagcc    360
acactttaaa gccatcatga tagcctcaaa cttaagagtt tccaaggtac agacaaaggt    420
gttgtcttcc tttagtacaa gtcgagtgcc attttcagac tttatgaagt atttaaattg    480
gatgatattt gacgatattg aaaactcctc tggaaatcca tccagcctgc ttttggacac    540
cagaacaatg cgagactta tttttgatat gaaatcagga gcattacaga agattcttaa    600
tccttgtgaa cgatcgtggt tatctgttat ttccaagaaa gtagtctctc tgggtgttag    660
ctgttctttc tcccacctgg atntcacttc ctctgccagt cncttgagct gaaagattct    720
gc                                                                  722
```

<210> SEQ ID NO 4
<211> LENGTH: 586
<212> TYPE: PRT
<213> ORGANISM: Human herpesvirus 5

<400> SEQUENCE: 4

```
Met Pro Arg Val Asp Pro Asn Leu Arg Asn Arg Ala Arg Pro Arg
1               5                   10                  15

Ala Arg Arg Gly Gly Gly Gly Val Gly Ser Asn Ser Ser Arg His
                20                  25                  30

Ser Gly Lys Cys Arg Arg Gln Arg Arg Ala Leu Ser Ala Pro Pro Leu
            35                  40                  45

Thr Phe Leu Ala Thr Thr Thr Thr Thr Met Met Gly Val Ala Ser
    50                  55                  60

Thr Asp Asp Asp Ser Leu Leu Leu Lys Thr Pro Asp Glu Leu Asp Lys
65                  70                  75                  80

Tyr Ser Gly Ser Pro Gln Thr Ile Leu Thr Leu Thr Asp Lys His Asp
                85                  90                  95

Ile Arg Gln Pro Arg Val His Arg Gly Thr Tyr His Leu Ile Gln Leu
            100                 105                 110

His Leu Asp Leu Arg Pro Glu Glu Leu Arg Asp Pro Phe Gln Ile Leu
        115                 120                 125

Leu Ser Thr Pro Leu Gln Leu Gly Glu Ala Asn Asp Glu Ser Gln Thr
```

```
            130                 135                 140
Ala Pro Ala Thr Leu Gln Glu Glu Thr Ala Ala Ser His Glu Pro
145                 150                 155                 160

Glu Lys Lys Lys Glu Lys Gln Glu Lys Lys Glu Glu Asp Glu Asp
                165                 170                 175

Arg Asn Asp Asp Arg Glu Arg Gly Ile Leu Cys Val Val Ser Asn Glu
            180                 185                 190

Asp Ser Asp Val Arg Pro Ala Phe Ser Leu Phe Pro Ala Arg Pro Gly
            195                 200                 205

Cys His Ile Leu Arg Ser Val Ile Asp Gln Gln Leu Thr Arg Met Ala
            210                 215                 220

Ile Val Arg Leu Ser Leu Asn Leu Phe Ala Leu Arg Ile Ile Thr Pro
225                 230                 235                 240

Leu Leu Lys Arg Leu Pro Leu Arg Arg Lys Ala Ala His His Thr Ala
                245                 250                 255

Leu His Asp Cys Leu Ala Leu His Leu Pro Glu Leu Thr Phe Glu Pro
            260                 265                 270

Thr Leu Asp Ile Asn Asn Val Thr Glu Asn Ala Ala Ser Val Ala Asp
            275                 280                 285

Thr Ala Glu Ser Thr Asp Ala Asp Leu Thr Pro Thr Leu Thr Val Arg
290                 295                 300

Val Arg His Ala Leu Cys Trp His Arg Val Glu Gly Ile Ser Gly
305                 310                 315                 320

Pro Arg Gly Leu Thr Ser Arg Ile Ser Ala Arg Leu Ser Glu Thr Thr
                325                 330                 335

Ala Lys Thr Leu Gly Pro Ser Val Phe Gly Arg Leu Glu Leu Asp Pro
            340                 345                 350

Asn Glu Ser Pro Pro Asp Leu Thr Leu Ser Ser Leu Thr Leu Tyr Gln
            355                 360                 365

Asp Gly Ile Leu Arg Phe Asn Val Thr Cys Asp Arg Thr Glu Ala Pro
            370                 375                 380

Ala Asp Pro Val Ala Phe Arg Leu Arg Leu Arg Arg Glu Thr Val Arg
385                 390                 395                 400

Arg Pro Phe Phe Ser Asp Ala Pro Leu Pro Tyr Phe Val Pro Pro Arg
                405                 410                 415

Ser Gly Ala Ala Asp Glu Gly Leu Glu Val Arg Val Pro Tyr Glu Leu
            420                 425                 430

Thr Leu Lys Asn Ser His Thr Leu Arg Ile Tyr Arg Arg Phe Tyr Gly
            435                 440                 445

Pro Tyr Leu Gly Val Phe Val Pro His Asn Arg Gln Gly Leu Lys Met
            450                 455                 460

Pro Val Thr Val Trp Leu Pro Arg Ser Trp Leu Glu Leu Thr Val Leu
465                 470                 475                 480

Val Ser Asp Glu Asn Gly Ala Thr Phe Pro Arg Asp Ala Leu Leu Gly
                485                 490                 495

Arg Leu Tyr Phe Ile Ser Ser Lys His Thr Leu Asn Arg Gly Cys Leu
            500                 505                 510

Ser Ala Met Thr His Gln Val Lys Ser Thr Leu His Ser Arg Ser Thr
            515                 520                 525

Ser His Ser Pro Ser Gln Gln Gln Leu Ser Val Leu Gly Ala Ser Ile
            530                 535                 540

Ala Leu Glu Asp Leu Leu Pro Met Arg Leu Ala Ser Pro Glu Thr Glu
545                 550                 555                 560
```

```
Pro Gln Asp Cys Lys Leu Thr Glu Asn Thr Thr Glu Lys Thr Ser Pro
                565                 570                 575
Val Thr Leu Ala Met Val Cys Gly Asp Leu
            580                 585

<210> SEQ ID NO 5
<211> LENGTH: 144
<212> TYPE: DNA
<213> ORGANISM: Homo sapiens

<400> SEQUENCE: 5
ggaaccaatc caaatgccca tcaatgatag actagataaa gaaaatatag tacatatgca      60
ccatgtaata ctatgcagcc gtaaaaaaaa aaaaaaaaaa agacagacaa ggccaaggcc     120
aggcacggtg ggtaaaaaaa aaaa                                           144
```